(12) United States Patent
Davies-Smith et al.

(10) Patent No.: US 11,484,112 B2
(45) Date of Patent: Nov. 1, 2022

(54) METHOD OF WHITENING TEETH

(71) Applicant: Colgate-Palmolive Company, New York, NY (US)

(72) Inventors: Leighton Davies-Smith, Lebanon, NJ (US); Erin Speicher, Hoboken, NJ (US)

(73) Assignee: Colgate-Palmolive Company, New York, NY (US)

( * ) Notice: Subject to any disclaimer, the term of this patent is extended or adjusted under 35 U.S.C. 154(b) by 279 days.

(21) Appl. No.: 16/188,520

(22) Filed: Nov. 13, 2018

(65) Prior Publication Data

US 2020/0146431 A1 May 14, 2020

(51) Int. Cl.
| | | |
|---|---|---|
| A46B 11/00 | (2006.01) | |
| A46B 9/06 | (2006.01) | |
| A61K 8/22 | (2006.01) | |
| A46D 1/00 | (2006.01) | |

(52) U.S. Cl.
CPC .............. *A46B 11/001* (2013.01); *A46B 9/06* (2013.01); *A46B 11/0082* (2013.01); *A46D 1/0207* (2013.01); *A61K 8/22* (2013.01); *A46B 2200/1066* (2013.01); *A61K 2800/87* (2013.01)

(58) Field of Classification Search
CPC ..... A46B 11/001; A46B 11/0082; A46B 9/06; A46B 2200/1066; A46D 1/0207; A61K 8/22; A61K 2800/87
See application file for complete search history.

(56) References Cited

U.S. PATENT DOCUMENTS

| | | | |
|---|---|---|---|
| 1,030,383 A | 6/1912 | Hunt | |
| 1,798,081 A | 3/1931 | Gordyn, Jr. et al. | |
| 2,594,721 A | 4/1952 | Beebe | |
| 3,465,376 A * | 9/1969 | Smith ................. | A46B 11/063 |
| | | | 15/104.92 |
| 4,517,701 A | 5/1985 | Stanford, Jr. | |
| 4,776,500 A | 10/1988 | Ford | |
| 4,849,213 A | 7/1989 | Schaeffer | |
| 5,033,898 A | 7/1991 | Williams | |
| 5,061,106 A | 10/1991 | Kent | |
| 5,062,728 A | 11/1991 | Kuo | |
| 5,096,319 A | 3/1992 | Gueret | |
| 5,276,935 A | 1/1994 | Lemon et al. | |
| 5,309,590 A | 5/1994 | Giuliani et al. | |
| 5,439,014 A | 8/1995 | Moussa | |
| 5,476,384 A | 12/1995 | Giuliani et al. | |

(Continued)

FOREIGN PATENT DOCUMENTS

| | | |
|---|---|---|
| DE | 451728 C | 11/1927 |
| JP | S58-163309 A | 9/1983 |

(Continued)

*Primary Examiner* — Nicholas D Lucchesi
*Assistant Examiner* — Hao D Mai

(57) ABSTRACT

A method of whitening teeth. The method may include delivering a buffer solution from a reservoir of a toothbrush to one or more tooth cleaning elements of the toothbrush; applying a toothpaste containing a peroxide to the tooth cleaning elements, the toothpaste having a first pH; and brushing the teeth with the tooth cleaning elements, thereby mixing the buffer solution and the toothpaste to form, at surfaces of the teeth, a tooth whitening mixture having a second pH that is greater than the first pH.

13 Claims, 24 Drawing Sheets

(56) References Cited

U.S. PATENT DOCUMENTS

| | | | |
|---|---|---|---|
| 5,611,687 A | 3/1997 | Wagner | |
| 5,902,568 A | 5/1999 | Ryles et al. | |
| 6,085,379 A | 7/2000 | Stafford | |
| 6,108,850 A * | 8/2000 | McLaughlin | A46B 11/0003 132/308 |
| 6,123,477 A | 9/2000 | Hecker | |
| 6,158,442 A | 12/2000 | Piatetsky | |
| 6,164,967 A | 12/2000 | Sale et al. | |
| 6,257,791 B1 | 7/2001 | Scamard | |
| 6,315,556 B1 | 11/2001 | Stewart | |
| 6,322,268 B1 * | 11/2001 | Kaufmann | B43K 8/02 401/198 |
| 6,345,405 B1 | 2/2002 | Brackin | |
| 6,648,641 B1 | 11/2003 | Viltro et al. | |
| 6,726,386 B1 * | 4/2004 | Gruenbacher | A47L 13/18 401/7 |
| 7,036,179 B1 | 5/2006 | Weihrauch | |
| 7,055,528 B2 | 6/2006 | Shah et al. | |
| 7,331,731 B2 | 2/2008 | Hohlbein et al. | |
| 7,641,410 B2 | 1/2010 | Frazell | |
| 7,789,583 B2 | 9/2010 | Kuo | |
| 7,845,360 B2 | 12/2010 | Walters et al. | |
| 8,109,686 B2 | 2/2012 | Bartschi, et al. | |
| 8,398,325 B2 | 3/2013 | Wu et al. | |
| 8,398,326 B2 | 3/2013 | Jimenez et al. | |
| 8,517,728 B2 | 8/2013 | Gatzemeyer et al. | |
| 9,033,602 B2 | 5/2015 | Boyd et al. | |
| 9,402,700 B2 | 8/2016 | Patel et al. | |
| 9,427,079 B2 | 8/2016 | Korup | |
| 9,554,641 B2 * | 1/2017 | Worthington | A46B 15/0081 |
| 9,848,693 B2 * | 12/2017 | Jimenez | A46B 11/0062 |
| 2003/0228264 A1 * | 12/2003 | Perna | A61K 8/22 424/53 |
| 2004/0255416 A1 | 12/2004 | Hohlbein | |
| 2007/0015112 A1 * | 1/2007 | Hochman | A61B 8/546 433/215 |
| 2007/0254260 A1 * | 11/2007 | Alden | A61C 17/22 433/85 |
| 2008/0060153 A1 | 3/2008 | Jansheski | |
| 2009/0060622 A1 * | 3/2009 | Lian | A61C 17/3445 401/28 |
| 2009/0070949 A1 * | 3/2009 | Sagel | A46B 11/0058 15/28 |
| 2009/0253101 A1 * | 10/2009 | Arnold | A61P 1/02 433/216 |
| 2009/0297253 A1 | 12/2009 | Yuu | |
| 2011/0067732 A1 * | 3/2011 | Smith | C02F 1/42 134/10 |
| 2011/0257060 A1 * | 10/2011 | Dykstra | C11D 3/3956 510/293 |
| 2014/0124514 A1 * | 5/2014 | Stepovich | A61J 1/201 220/625 |
| 2015/0320193 A1 * | 11/2015 | Tatu | A46B 11/0024 15/105 |
| 2017/0007215 A1 * | 1/2017 | Podoly | A61C 19/04 |
| 2017/0042648 A1 | 2/2017 | Zachar et al. | |
| 2017/0135464 A1 * | 5/2017 | Knickerbocker | A46B 15/0004 |
| 2018/0168328 A1 | 6/2018 | Davies-Smith et al. | |
| 2018/0168329 A1 | 6/2018 | Davies-Smith et al. | |
| 2018/0168330 A1 | 6/2018 | Davies-Smith et al. | |

FOREIGN PATENT DOCUMENTS

| | | |
|---|---|---|
| JP | H04-215706 A | 8/1992 |
| JP | H06-90824 A | 4/1994 |
| WO | 2017/116400 | 7/2017 |

* cited by examiner

METHOD OF WHITENING TEETH

BACKGROUND

Personal care implements used for grooming and hygiene are well known. Furthermore, personal care implements that dispense a fluid are also known. For example, oral care implements or toothbrushes exist the dispense a fluid such as a dentifrice so that a user does not need to worry about applying dentifrice to the bristles as a separate step in an oral hygiene regimen. However, such existing oral care implements suffer from deficiencies, such as clogging of the fluid channels, the fluid drying out, mechanisms used for fluid transport malfunctioning, and the like. Thus, a need exists for a personal care implement that can dispense a fluid that overcomes the noted deficiencies. Furthermore, it is known that toothpaste formulations that include hydrogen peroxide are maintained at a pH that is lower than the optimal pH for tooth whitening in order to maximize the shelf life of the hydrogen peroxide containing formulation. Thus, a need exists to increase the pH of such toothpastes prior to or during application to a user's teeth. Finally, toothbrushes are known to harbor bacteria and while rinsing before and after brushing removes some of these bacteria, it does not remove it all. Thus, a need exists for a toothbrush having a self-sanitizing feature.

BRIEF SUMMARY

The present invention is directed to a personal care implement that is capable of dispensing a fluid to the elements of the personal care implement that are intended to interact with a person. For example, if the personal care implement is a toothbrush, it delivers a fluid to the tooth cleaning elements or bristles. If the personal care implement is a hairbrush, it may passively a fluid to the brush members. In the case of a toothbrush, the bristles are not hollow, but rather the fluid is delivered, via a wicking action, into the spaces between the individual filaments that make up each bristle tuft. The invention is also directed to a method for preparing a toothbrush for cleaning an oral cavity, a method of whitening teeth, and a method of sanitizing a toothbrush.

In one aspect, the invention may be an oral care implement comprising: a body comprising a handle and a head; at least one reservoir containing a store of a first fluid in the body; a plurality of bristle tufts coupled to the head, each of the bristle tufts extending along an axis and comprising a plurality of bristle filaments; at least one capillary member having a first portion that is fluidly coupled to the store of the first fluid and a second portion that is in continuous physical contact with a bottom end of at least a first bristle tuft of the plurality of bristle tufts; wherein the at least one capillary member is configured to deliver the first fluid from the reservoir to the bottom end of the first bristle tuft via capillary action; and wherein the first bristle tuft is configured so that the first fluid flows axially along the first bristle tuft through spaces between the bristle filaments of the first bristle tuft from the bottom end of the first bristle tuft toward a distal end of the first bristle tuft via capillary action.

In another aspect, the invention may be an oral care implement comprising: a head; a plurality of bristle tufts coupled to the head, the plurality of bristle tufts comprising a first subset of bristle tufts and a second subset of bristle tufts; at least one reservoir containing a store of a fluid; each bristle tuft of the first subset of bristle tufts fluidly coupled to the reservoir and configured to deliver the fluid to a distal end of the bristle tuft; and each bristle tuft of the second subset of bristle tufts fluidly isolated from the reservoir.

In yet another aspect, the invention may be an oral care implement comprising: a body comprising a handle and a head; at least one reservoir containing a store of a fluid in the body; a plurality of bristle tufts coupled to the head, each of the bristle tufts comprising a plurality of bristle filaments; at least one capillary member that is fluidly coupled to the store of the first fluid and to at least a first bristle tuft of the plurality of bristle tufts; and wherein the at least one capillary member has a first capillarity and the first bristle tuft has a second capillarity, the second capillarity being greater than the first capillarity so that the fluid is delivered, via capillary action, from the reservoir to the first bristle tuft.

In still another aspect, the invention may be a method of whitening teeth comprising: providing a toothbrush comprising a reservoir containing a store of a buffer solution and a plurality of tooth cleaning elements; delivering the buffer solution from the reservoir to one or more of the tooth cleaning elements; applying a toothpaste containing a peroxide to the tooth cleaning elements of the toothbrush, the toothpaste having a first pH; and brushing the teeth with the tooth cleaning elements, thereby mixing the buffer solution and the toothpaste to form, at surfaces of the teeth, a tooth whitening mixture having a second pH that is greater than the first pH.

In a further aspect, the invention may be a method of whitening teeth comprising: providing a toothbrush comprising a reservoir containing a store of a buffer solution and a head having an applicator; delivering the buffer solution from the reservoir to the applicator; applying a toothpaste containing a peroxide to tooth cleaning elements of the toothbrush, the toothpaste having a first pH; and brushing teeth with the tooth cleaning elements, thereby mixing the buffer solution and the toothpaste to form, at surfaces of the teeth, a tooth whitening mixture having a second pH that is greater than the first pH.

In a still further aspect, the invention may be a method of sanitizing a toothbrush comprising: delivering a sanitizing fluid from a reservoir of a toothbrush that comprises a store of the sanitizing fluid to bristle tufts of the toothbrush solely via capillary action, wherein each of the bristle tufts comprises a plurality of bristle filaments so that the sanitizing fluid wicks upwardly along the bristle tufts within spaces between the bristle filaments to sanitize the bristle filaments.

In another aspect, the invention may be a method of sanitizing a toothbrush in between toothbrushing sessions, the method comprising: after a first toothbrushing session, delivering a sanitizing fluid from a reservoir of a toothbrush that comprises a store of the sanitizing fluid to bristle tufts of the toothbrush solely via capillary action to sanitize the bristle tufts; applying a toothpaste to the bristle tufts of the toothbrush; conducting a second toothbrushing session with the bristle tufts having the toothpaste thereon; and after completion of the second toothbrushing session, allowing the toothbrush to rest idly for a period of time during which the sanitizing fluid is delivered from the reservoir to the bristle tufts via capillary action to sanitize the bristle tufts in between toothbrushing sessions.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
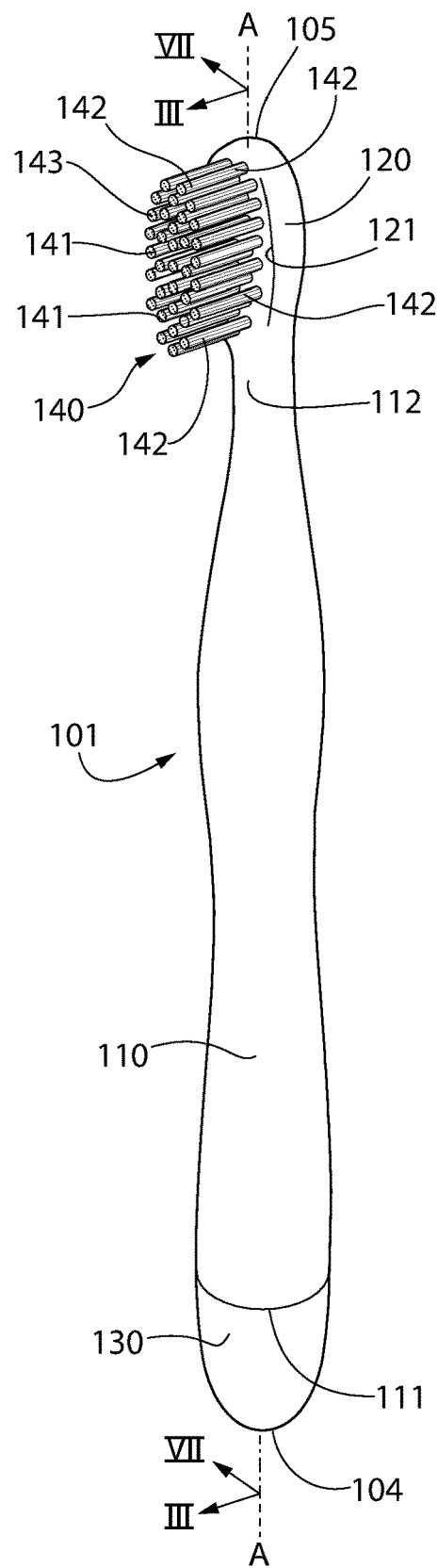
FIG. 1 is front perspective view of a personal care implement in accordance with an embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Figure 2:
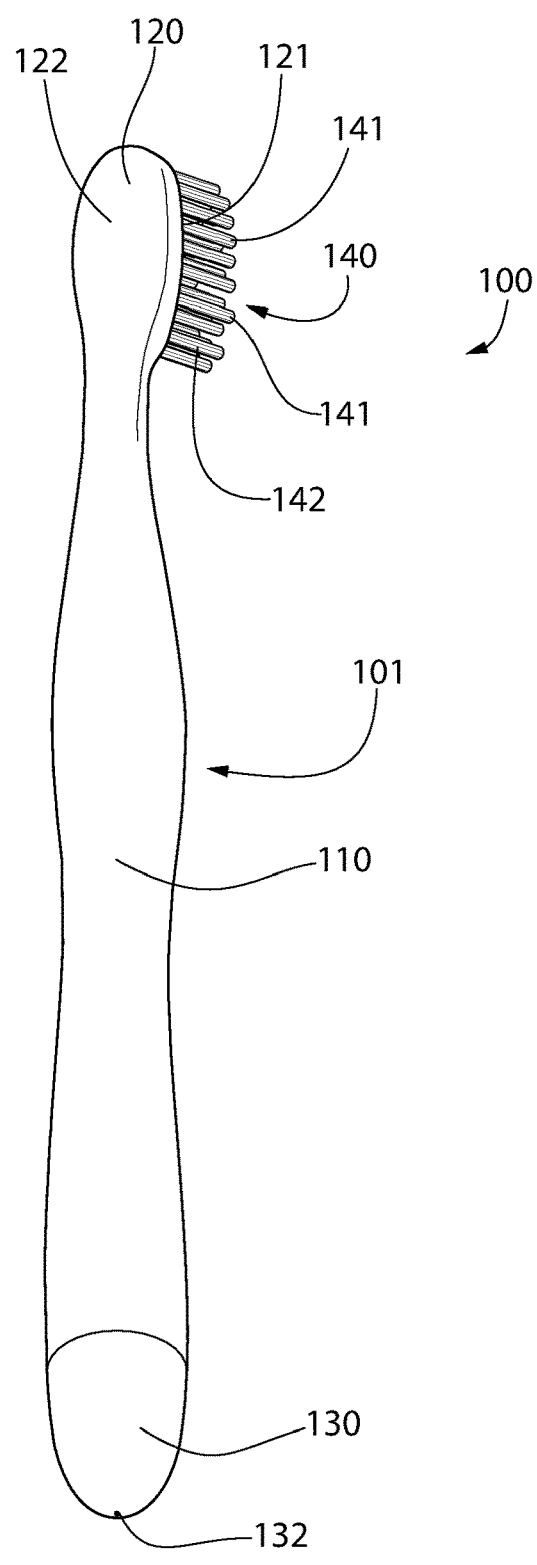
FIG. 2 is a rear perspective view of the personal care implement of FIG. 1.
Figure 3:
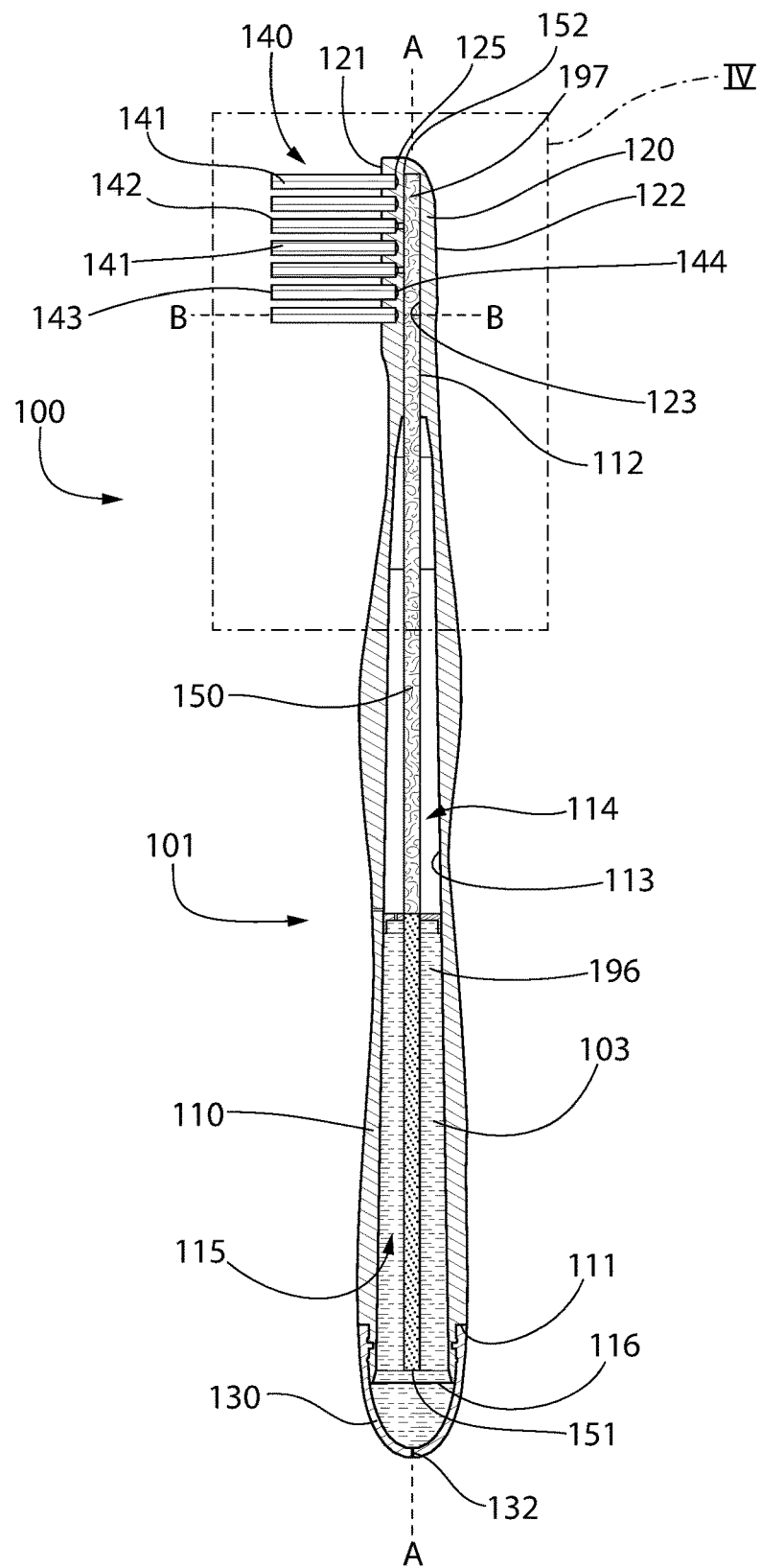
FIG. 3 is a cross-sectional view taken along line of FIG. 1.

Referring first to FIGS. 1-3, a personal care implement 100 is illustrated in accordance with an embodiment of the present invention. In the exemplified embodiment, the personal care implement 100 is an oral care implement, and more specifically a manual toothbrush. Thus, the invention will be described herein with the details predominately directed to a toothbrush. However, in certain other embodiments the personal care implement 100 can take on other forms such as being a powered toothbrush, a tongue scraper, a gum and soft tissue cleanser, a water pick, an interdental device, a tooth polisher, a specially designed ansate implement having tooth engaging elements, a hairbrush, a razor or any other type of implement that is commonly used for personal care. For example, the personal care implement 100 may not be one that is specifically used for oral care in all embodiments, but rather it may be an implement such as a deodorant application implement, a face or body cleaning implement, a make-up applicator implement, a razor or shaving implement, a hairbrush, or the like. Thus, it is to be understood that the inventive concepts discussed herein can be applied to any type of personal care implement unless a specific type of personal care implement is specified in the claims.

In the exemplified embodiment, the personal care implement 100 generally includes a body 101 comprising a handle 110 and a head 120 and an end cap 130 that is detachably coupled to the handle 110. The personal care implement 100 generally extends along a longitudinal axis A-A from a proximal end 104 to a distal end 105. Conceptually, the longitudinal axis A-A is a reference line that is generally coextensive with the three-dimensional center line of the body 101. Because the body 101 may, in certain embodiments, be a non-linear structure, the longitudinal axis A-A of the body 101 may also be non-linear in certain embodiments. However, the invention is not to be so limited in all embodiments and in certain other embodiments the body 101 may have a simple linear arrangement and thus a substantially linear longitudinal axis A-A.

The handle 110 extends from a proximal end 111 to a distal end 112 and the head 120 is coupled to the distal end 112 of the handle 110. In the exemplified embodiment, the end cap 130 is detachably coupled to the proximal end 111 of the handle 120. Specifically, the handle 120 has an opening 116 at the proximal end 111 thereof and the end cap 130 is coupled to the proximal end 111 of the handle 120 and closes the opening 116. The end cap 130 may be detachable from the handle 120 so that a fluid such as an oral care material can be stored within the body 101 and can be refilled by detaching the end cap 130 from the handle 110 to provide access, via the opening 116, to a cavity/reservoir within the body 101 within which the fluid may be stored. An air vent 132 may be formed into the end cap 130 or at other locations along the body 101 that are aligned with a reservoir containing a fluid, as described in more detail below. Furthermore, in certain embodiments the end cap 130 may be altogether omitted and the proximal end 111 of the body 101 may form a closed bottom end of the personal care implement 100. In such embodiments, refill of the reservoir may not be possible or may occur through other mechanisms/structures as would be understood to persons skilled in the art, such as openings located elsewhere along the body 101. In some embodiments, refilling the fluid may not be desirable because the fluid may be intended to last for the same length of time as the bristles (approximately three months), and thus once the fluid has been used up it is time to replace the personal care implement 100.

The handle 110 is an elongated structure that provides the mechanism by which the user can hold and manipulate the personal care implement 100 during use. In the exemplified embodiment, the handle 110 is generically depicted having various contours for user comfort. Of course, the invention is not to be so limited in all embodiments and in certain other embodiments the handle 110 can take on a wide variety of shapes, contours and configurations, none of which are limiting of the present invention unless so specified in the claims.

In the exemplified embodiment, the handle 110 is formed of a rigid plastic material, such as, for example without limitation, polymers and copolymers of ethylene, propylene, butadiene, vinyl compounds, and polyesters such as polyethylene terephthalate. Furthermore, although not shown in the exemplified embodiment, the handle 110 may include a resilient material, such as a thermoplastic elastomer, as a grip cover that is molded over portions of or the entirety of the rigid plastic material to enhance the gripability of the handle 110 during use. For example, portions of the handle 110 that are typically gripped by a user's palm and/or thumb and forefinger during use may be overmolded with a thermoplastic elastomer or other resilient material to further increase comfort to a user.

The head 120 of the personal care implement 100 is coupled to the handle 110 and comprises a front surface 121 and a rear surface 122 opposite the front surface 121. In the exemplified embodiment, the head 120 is formed integrally with the handle 110 as a single unitary structure using a molding, milling, machining or other suitable process. However, in other embodiments the handle 110 and the head 120 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. In some embodiments, the head 120 may be detachable from the handle 110. The head 120 may be formed of any one of the materials discussed above with regard to the handle 110.

In the exemplified embodiment, a plurality of cleaning elements 140 are coupled to the head 120 and extend from the front surface 121 of the head 120. In the exemplified embodiment whereby the personal care implement 100 is a toothbrush, the cleaning elements 140 are elements specifically designed for tooth cleaning (i.e., bristles, lamella, or the like). Of course, depending on the particular type of device selected for the personal care implement 100, the cleaning elements 140 may be replaced with other types of elements (for example, when the personal care implement 100 is a hairbrush or a mascara applicator). The cleaning elements 140 may be arranged on the head 120 in any desired pattern, including being a symmetrical collection of rows/columns of cleaning elements, unevenly spaced apart cleaning elements, or the like.

In the exemplified embodiment, the cleaning elements 140 comprises a plurality of bristle tufts 141. Each of the bristle tufts 141 extends from the front surface 121 of the head 120 along an axis B-B. In some embodiments, the axis B-B may be perpendicular to the axis A-A and the bristle tufts 141 may extend perpendicularly from the front surface 121 of the head 120. However, the invention is not to be so limited in all embodiments and the bristle tufts 141 may extend at an angle relative to the front surface 121 of the head 120 in other embodiments. Thus, one or more of the bristle tufts 141 may be angled towards the distal end 105 of the body 101, towards the proximal end 104 of the body 101, towards the side edges of the head 120, or in any other desired manner. In some embodiments, some of the bristle tufts 141 may be oriented perpendicularly relative to the front surface 121 of the head 120 and others of the bristle tufts 141 may be oriented at an angle relative to the front surface 121 of the head 120. Each of the bristle tufts 141 extends from a bottom end 144 that is located within a tuft hole 125 to a distal end 143 that is at a predetermined distance from the front surface 121 of the head 120. The bristle tufts 141 may all have the same height, or the personal care implement 100 may include bristle tufts 141 of varying height as may be desired.

The bristle tufts 141 are separate from one another, with each bristle tuft 141 being disposed within its own tuft hole 125 formed in the front surface 121 of the head 120. Of course, adjacently positioned bristle tufts 141 or portions thereof may contact one another, particularly near their distal ends 143 because the bristle tufts 141 may splay as they extend further from the head 120. In the exemplified embodiment, each of the bristle tufts 141 comprises a plurality of bristle filaments 142. In some embodiments, each of the bristle tufts 141 may consist only of a plurality of the bristle filaments 142. In other embodiments, some, but not necessarily all, of the bristle tufts 141 may consist only of a plurality of the bristle filaments 142. The bristle filaments 142 are arranged in the bristle tuft 141 such that at least some of the bristle filaments 142 within each bristle tuft 141 are spaced apart from one another (see, for example, FIG. 4E). Although some of the bristle filaments 142 within each particular bristle tuft 141 may be in contact with some of the other bristle filaments 142 within that same bristle tuft 141, as a general matter there will be spaces that exist along the length of the bristle tuft 141 from the bottom end 144 of the bristle tuft 141 to the distal end 143 of the bristle tuft 141 for each of the bristle tufts 141. The spaces are air gaps between the bristle filaments 142 and they may be quite small and each bristle tuft 141 may comprise spaces of varying width, diameter, thickness, or the like.

In the exemplified embodiment, each of the bristle tufts 141 has a cylindrical shape with a round transverse cross-sectional shape. However, the invention should not be so limited in all embodiments and the bristle tufts 141 can take on any desired shapes. For example, in some embodiments some of the bristles tufts 141 may have an arcuate shape while others are cylindrical in shape. In still other embodiments, some of the bristle tufts 141 may have non-circular transverse cross-sectional shapes, such as being triangular, square, rectangular, diamond-shaped, or the like. The bristle tufts 141 may all have the same shape or there may be a collection of bristle tufts 141 having different shapes that collectively make up the cleaning elements 140.

In the exemplified embodiment, the bristle filaments 142 may be formed of a material that is conventionally used as the bristles on a toothbrush. For example, the bristle filaments 142 may be formed from synthetic plastic materials such as, but not limited to, nylon, polyester, or a combination of both. Other materials that may be used for the bristle filaments 142 include polyethylene and polypropylene. Of course, natural materials such as animal hair (hog, badger, etc.) may also be used for the bristle filaments 142 in some embodiments. The bristle filaments 142 may be cylindrical and may have round, oval, triangular, diamond, square, or any other desired transverse cross-sectional shape. The bristle filaments 142 described herein may include end-rounded filaments, tapered bristles, multi-component filaments that form spiral bristles or core-sheath bristles, or the like. Thus, a single bristle tuft 141 may include only end-rounded bristles, only tapered bristles, only spiral bristles, only core-sheath bristles, or any of various combinations thereof. Furthermore, different ones of the bristle tufts 141 may include different ones of the types of bristle filaments 142 described herein, or they may all be the same. Furthermore, in the exemplified embodiment, the bristle filaments 142 are non-hollow, meaning that there is no passageway formed internally within the bristle filaments 142. Stated another way, the bristle filaments 142 are solid structures such that each individual filament bristle 142 does not have any cavities, passageways, or the like. The bristle filaments 142 are also formed entirely from a non-porous material (such as nylon) and are not coated in any way by a porous material. Thus, fluid cannot flow passively along the exterior of the individual bristle filaments 142 or within an interior cavity because one does not exist. Rather, fluid can only flow within spaces that exist between the bristle filaments 142 of a given bristle tuft 141.

Furthermore, although in the exemplified embodiment all of the cleaning elements 140 are bristle tufts 141 comprising (or consisting of) bristle filaments 142, the invention is not to be so limited in all embodiments. In other embodiments, some of the cleaning elements 140 may be bristle tufts 141 while others of the cleaning elements 140 may be elastomeric or rubber elements. Thus, the cleaning elements 140 may include a combination of elastomeric elements (i.e., lamella) and bristle tufts 141 comprising bristle filaments 142 to perform the cleaning function. Suitable elastomeric materials for such elastomeric elements include any bio-compatible resilient material suitable for uses in an oral hygiene apparatus. To provide optimum comfort as well as cleaning benefits, the elastomeric material of such elements may have a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The bristle tufts 141 may be coupled to the head 120 in any desired manner. For example, in accordance with the embodiment of FIGS. 1-3, the bristle tufts 141 may be coupled to the head 120 by folding a collection of the bristle filaments 142 in half to form a U-shaped bristle tuft, inserting the bight of the U-shaped bristle tuft into one of the tuft holes 125 in the head 120, and then stapling the bristle tufts 141 to the head 120 within the tuft hole 125. This is a conventional way of coupling the bristle tufts 141 to the head 120 and should be appreciated by persons skilled in the art. Of course, alternative processes are possible, one of which is anchor-free tufting, or AFT, which will be described in greater detail below with reference to FIG. 10.

Although not illustrated herein, in certain embodiments the head 120 may also include a soft tissue cleanser coupled to or positioned on its rear surface 122. An example of a suitable soft tissue cleanser that may be used with the present invention and positioned on the rear surface 122 of the head 120 is disclosed in U.S. Pat. No. 7,143,462, issued Dec. 5, 2006 to the assignee of the present application, the entirety of which is hereby incorporated herein by reference. In certain other embodiments, the soft tissue cleanser may include protuberances, which can take the form of elongated ridges, nubs, or combinations thereof. Of course, the invention is not to be so limited and in certain embodiments the personal care implement 100 may not include any soft tissue cleanser.

Figure 4A:
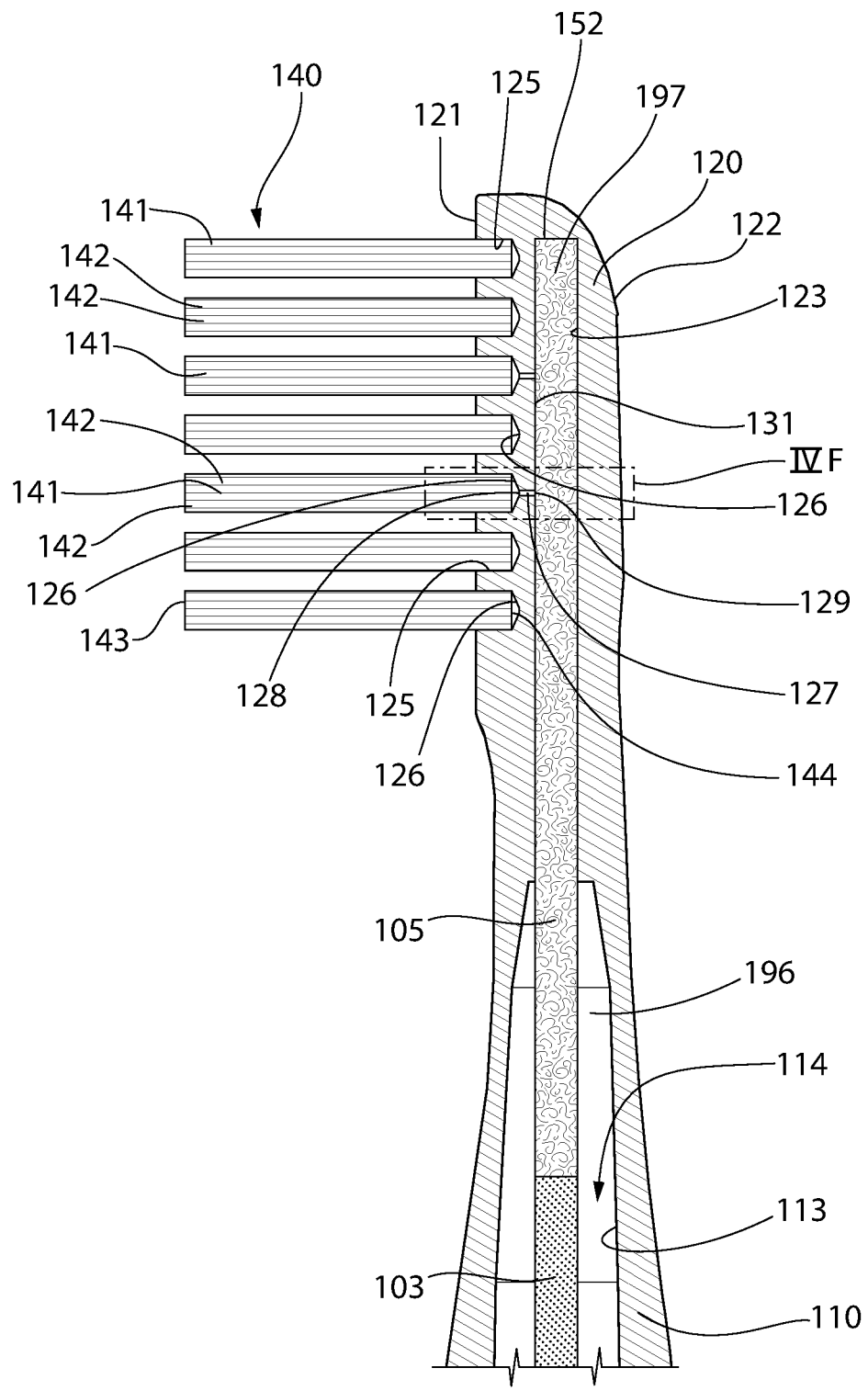
FIGS. 4A-4D are close-up views of area IV of FIG. 3 illustrating a process of a fluid being dispensed from a reservoir to bristles of the personal care implement.

Referring to FIGS. 3 and 4A, the personal care implement 100 will be described in greater detail. The body 101 comprises an inner surface 113 that defines a cavity 114. In the exemplified embodiment, the cavity 114 comprises a first portion 196 located in the handle 110 and a second portion 197 located in the head 120. The first and second portions 196, 197 of the cavity 114 are fluidly coupled together such that they collectively form a single uninterrupted volume of space, identified collectively as the cavity 114 of the body 101. In the exemplified, the first portion 196 of the cavity 114 comprises a reservoir 115 containing a store of a first fluid 103 located in the handle 110. However, the invention is not to be so limited in all embodiments and in certain other embodiments the second portion 197 of the cavity 114 may comprise the reservoir 115. In such an embodiment, the store of the first fluid 103 may be located entirely within the head 120 rather than being located within the handle 110. In still other embodiments, both of the first and second portions 196, 196 of the cavity 114 may form portions of the reservoir 115. Thus, the exact portion of the cavity 114 that forms the reservoir 115 is not to be limited to that which is depicted and any portion of the cavity 114 may form the reservoir 115.

One of the main functions of the personal care implement 100 is that the first fluid 103 can be transported/delivered from the reservoir 115 to the bristle tufts 141 for application of the first fluid 103 to a desired location on a user. This delivery of the fluid from the reservoir 115 to the bristle tufts 141 may occur naturally and passively due to capillary action. This means that in some embodiments no action is required by a user for this flow of the fluid, and no pumps or other mechanical structures are required. Rather, the fluid simply flows due to the components of the personal care implement 100 having characteristics that enable capillary action or wicking of the fluid. When the personal care implement 100 is a toothbrush, the first fluid 103 is transported/delivered to the bristle tufts 141 for application to a user's teeth and other oral cavity surfaces. When the personal care implement 100 is a hairbrush, the first fluid 103 may be transported/delivered to the bristle tufts 141 for application to a user's hair. Alternative uses are also possible as should be appreciated by persons skilled in the art.

To reiterate, the transport/delivery (or flow) of the first fluid 103 from the reservoir 115 to (and upwardly along) the cleaning elements 140 may be achieved, in some embodiments, in an entirely passive manner via capillary action. Thus, in some embodiments, there are no pumps (electrical or mechanical), valves or other mechanical devices included in the personal care implement 100. Rather, the fluid 103 merely flows via capillary action along capillary components from the reservoir 115 to the cleaning elements 140 and is then wicked upwardly along the cleaning elements 140 within the spaces between the bristle filaments 142. All of this flow/wicking action may occur naturally via capillary action without the need for a separate pump or any action on the part of the user. As noted above, the bristle filaments 142 are non-hollow and non-porous. Therefore, the first fluid 103 cannot pass through or along the individual bristle filaments 142 during this wicking action. Rather, the first fluid 103 wicks upwardly along the bristle tufts 141 within the spaces between the bristle filaments 142. This allows fluid delivery to or near the distal ends 143 of the bristle tufts 141 in a natural, passive manner while using traditional or conventional bristle filaments 142 to form the bristle tufts 141. This will be described in greater detail below with reference to FIGS. 4A-4E.

In certain embodiments, the first fluid 103 can be any fluid, particularly liquid, that is desired to be dispensed for application to a surface (such as a biological surface) depending on the end use. For example, when the desired application site is a user's oral cavity, the first fluid 103 may be one that provides a benefit to a user's oral surfaces (i.e., a benefit agent) such as a sensorial or therapeutic benefit. For example, without limitation, the first fluid 103 may be a mouthwash, a flavor agent, a dentifrice, a tooth whitening agent such as peroxide containing tooth whitening compositions, or the like. Other contemplated fluids that can be stored in the reservoir 115 include, for example without limitation, antibacterial agents; oxidative or whitening agents; enamel strengthening or repair agents; tooth erosion preventing agents; tooth sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents; dry mouth relief ingredients; catalysts to enhance the activity of any of these agents; colorants or aesthetic ingredients; and combinations thereof.

In certain embodiments the first fluid 103 may be free of (i.e., is not) toothpaste. Instead, the first fluid 103 in such embodiments is intended to provide benefits in addition to merely brushing one's teeth. Other suitable oral care materials could include lip balm or other materials that are typically available in a semi-solid state. Furthermore, in still other embodiments the first fluid 103 can be a natural ingredient, such as for example without limitation, lotus seed; lotus flower, bamboo salt; jasmine; corn mint; camellia; aloe; gingko; tea tree oil; xylitol; sea salt; vitamin C; ginger; cactus; baking soda; pine tree salt; green tea; white pearl; black pearl; charcoal powder; nephrite or jade and Ag/Au+. Furthermore, in embodiments that include multiple fluids (such as those described below with reference to FIGS. 6A-9C), each of the fluids described may be any one of the different materials described above.

In other embodiments, the first fluid 103 may be a buffer solution, such as Sodium bicarbonate ($NaHCO_3$) and sodium carbonate ($Na_2CO_3$). Such a buffer solution may be beneficial for use with a toothpaste containing hydrogen peroxide in order to raise the pH of the toothpaste to make the hydrogen peroxide more effective at tooth whitening. Of course, other types of peroxide or peroxide donors could be used and the invention is not limited to hydrogen peroxide. As used herein, stating that a toothpaste contains peroxide includes toothpastes that include hydrogen peroxide or other types of peroxide including peroxide donors. In still other embodiments, the first fluid 103 may be a sanitizing fluid to sanitize the cleaning elements 140 passively without any intervention or other action required by the user. The details of a personal care implement that uses a buffer solution or a sanitizing fluid as the first fluid 103 will be described in greater detail below.

In some embodiments, the fluid(s) to be delivered can be intended for cleaning, freshening, tooth whitening, gum line care, therapeutic benefit, or to provide a sensorial experience. Additionally, given that the delivered fluid(s) will be passively delivered through the tooth cleaning surface, the fluid(s) can also interact with a uniquely chosen toothpaste to deliver a combined or more efficacious benefit that would not be possible as individual components. Furthermore, another distinctive aspect of this invention is the unique capability to deliver the chosen liquid through specific bristle tufts rather than through all of the bristle tufts. This capability, which will be described in more detail below, can be leveraged to deliver a desired dosage of liquid during brushing, or to target a precise area of the mouth.

Thus, when the first fluid 103 is stored in an oral care implement or toothbrush, any of the above fluids may be desirable for use as the first fluid 103. In other embodiments the personal care implement 100 may not be a toothbrush. Thus, the first fluid 103 can be any other type of fluid that has beneficial results when dispensed in accordance with its end use or the end use of the product/implement with which it is associated. For example, the first fluid 103 may be hair gel or leave-in conditioner when the implement is a hairbrush, make-up (i.e., mascara or the like) when the implement is a make-up applicator, shaving cream when the implement is a razor, anti-acne cream when the implement is a skin or face scrubber, or the like.

The head 120 has an inner surface 123 that defines the second portion 197 of the cavity 114, which as described above extends internally within the head 120. As described above, the second portion 197 of the cavity 114 forms a part of the cavity 114 and thus the cavity 114 forms a singular, uninterrupted interior volume of space within the handle 110 and the head 120 (i.e., within the body 101). The second portion 197 of the cavity 114 is located within the head 120 beneath the cleaning elements 140 in such a manner that the second portion 197 of the cavity 114 is aligned with one or more of the cleaning elements 140. In some embodiments, the second portion 197 of the cavity 114 may comprise or form a part of the reservoir 115. In other embodiments, the second portion 197 of the cavity 114 may be considered to be a separate part of the cavity 114 relative to the reservoir 115.

Figure 4B:
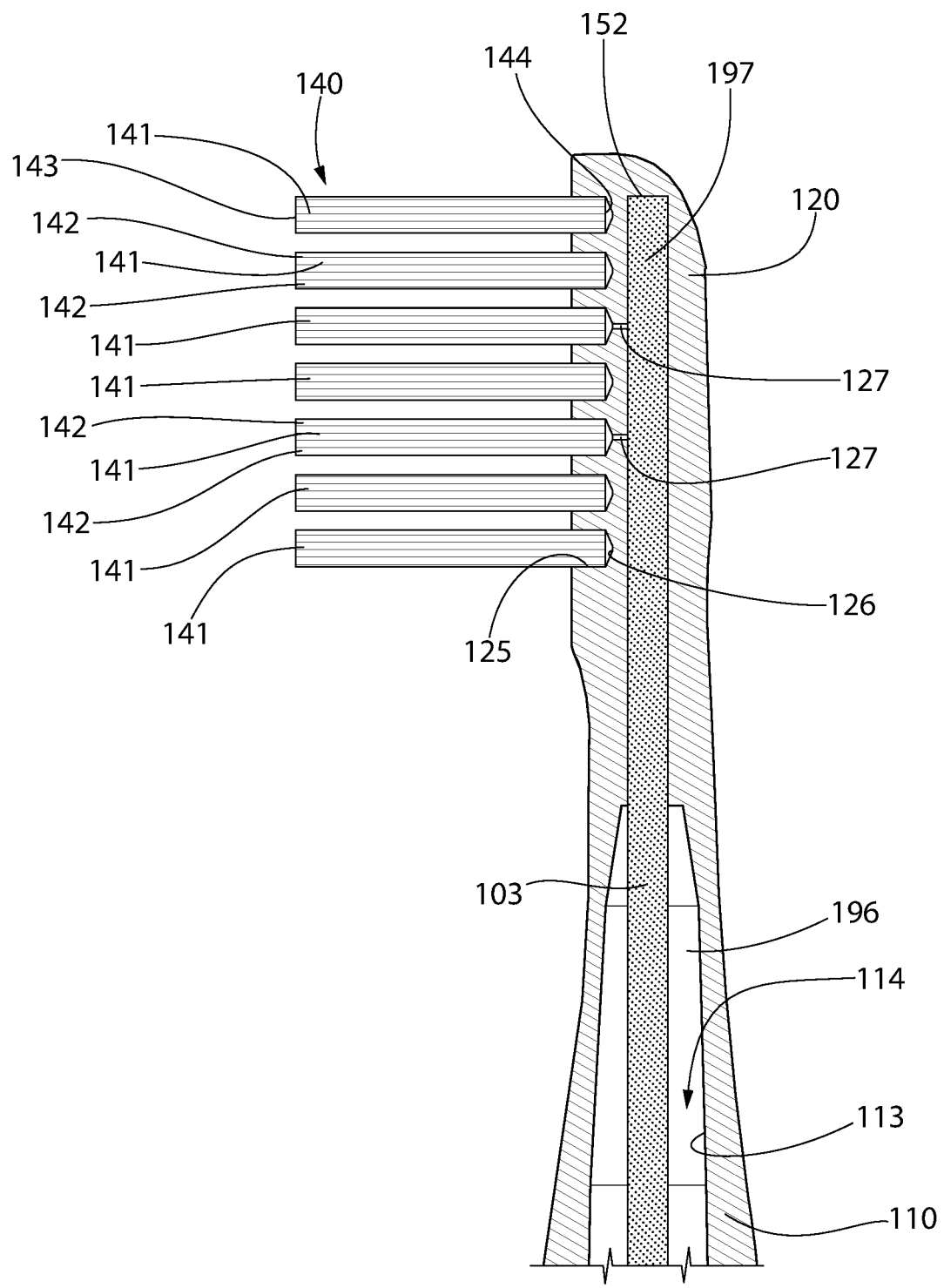
Figure 4C:
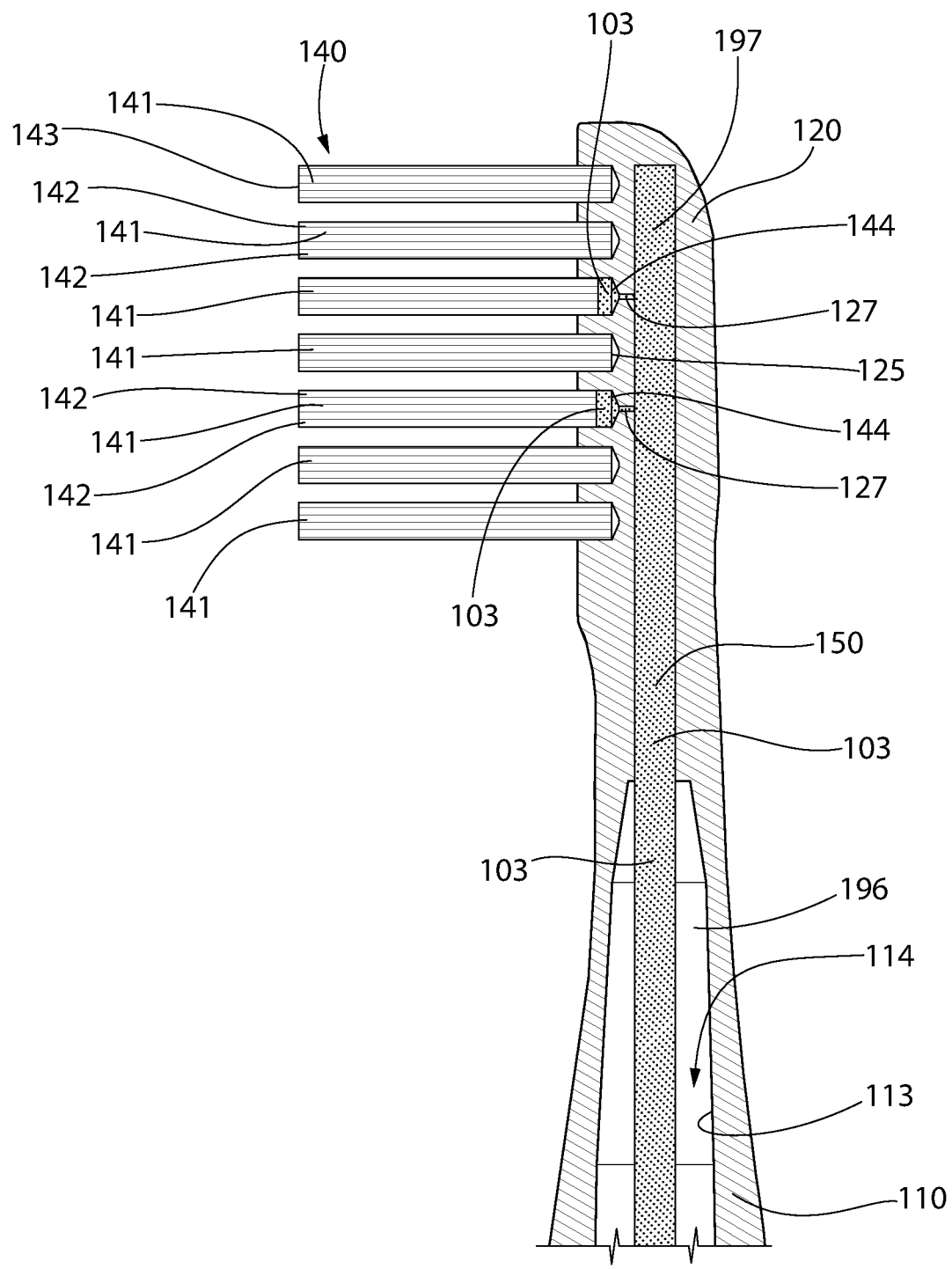
Figure 4D:
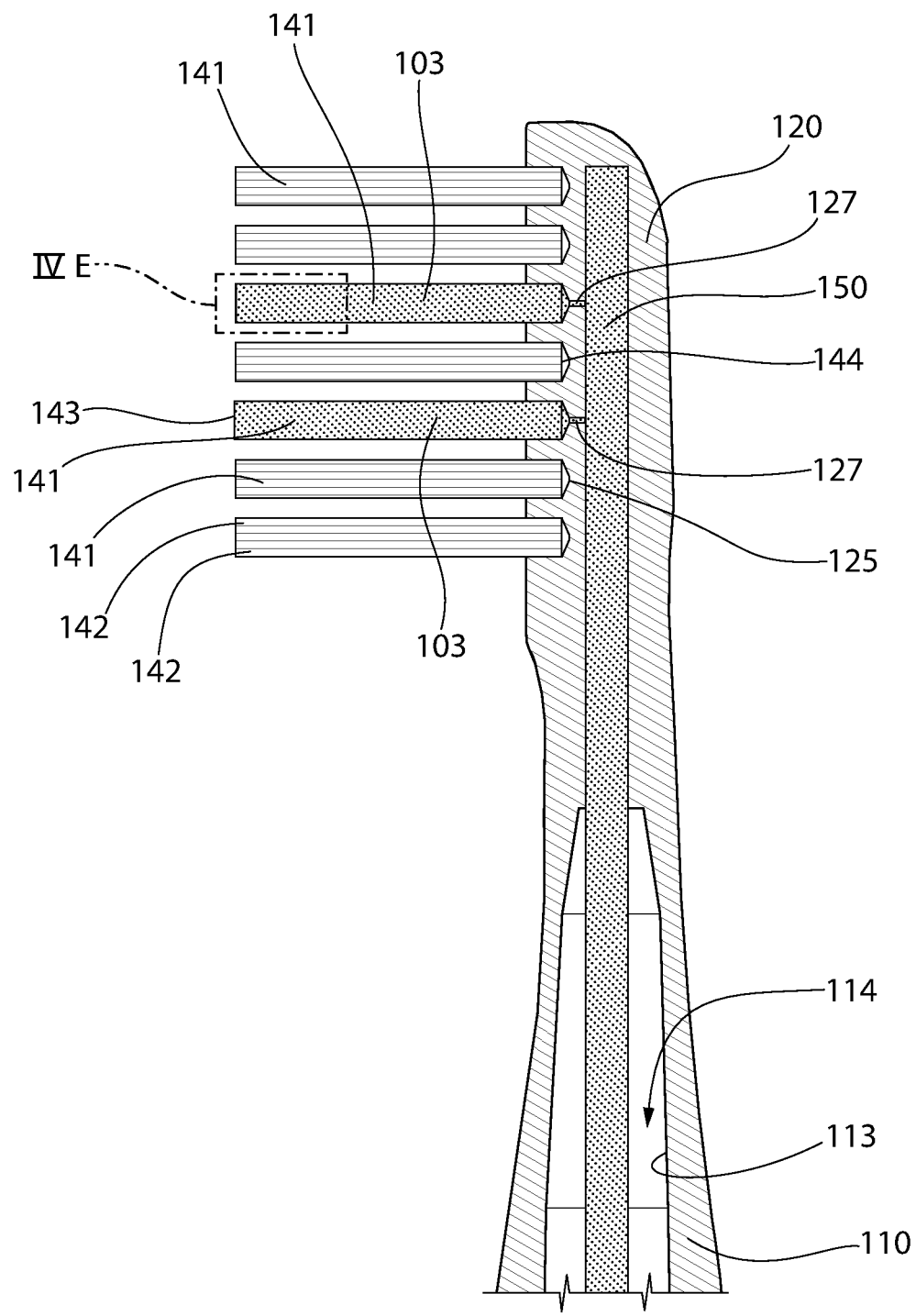
Figure 4E:
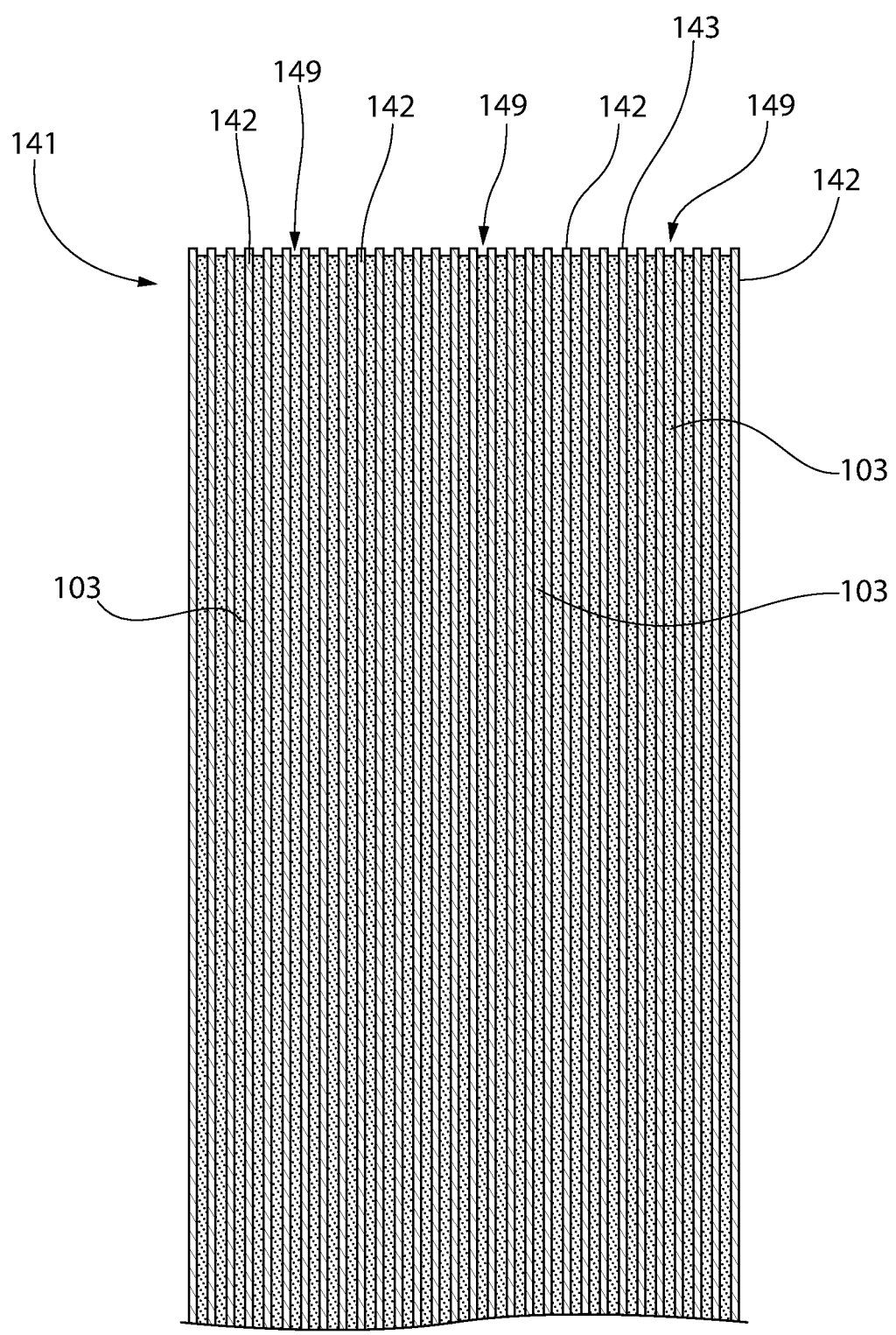
FIG. 4E is a close-up view of area IVE of FIG. 4D.
Figure 4F:
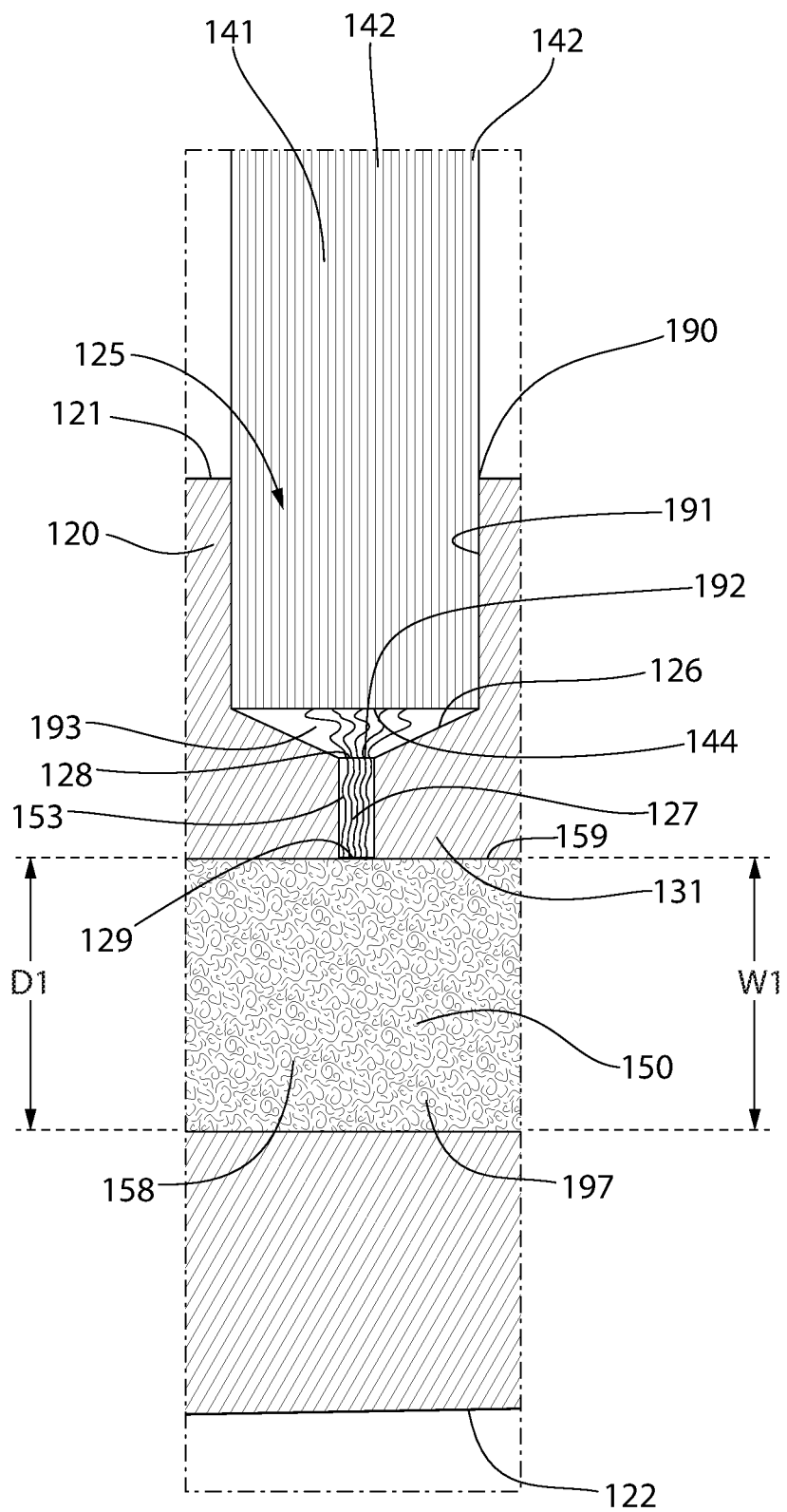
FIG. 4F is a close-up view of area IVF of FIG. 4A.

Referring to FIGS. 4A and 4F, as mentioned above, in the exemplified embodiment the head 120 comprises a plurality of tuft holes 125 such that one of the bristle tufts 141 is positioned within each of the tuft holes 125. Each of the tuft holes 125 has an opening 190 at the front surface 121 of the head 120 that permits the bristle tufts 141 (and a staple) to be inserted into the tuft hole 125. Furthermore, each of the tuft holes 125 comprises a floor 126 and a sidewall 191 extending from the floor 126 to the front surface 121 of the head 120. In the exemplified embodiment, the floor 126 is sloped such that the floor 126 is oriented obliquely relative to the sidewall 191. The floor 126 is sloped so that the floor 126 terminates in an apex 192. Furthermore, due to the sloping nature of the floor 126, the tuft hole 125 has a bottom portion 193 having a conical shape. Stated another way, in the exemplified embodiment, the floor 126 is V-shaped in cross-section, such that the bottom portion 193 of the tuft holes 125 is in the shape of a cone, or more specifically a truncated cone. Of course, the invention is not to be so limited and in other embodiments the floor 126 could be planar and parallel to the front surface 121 of the head 120 or the floor 126 could be rounded so as to be concave, convex, wavy, or the like. However, the conical-shaped bottom portion may be desirable in some embodiments to enhance the wicking or capillary flow of the first fluid 103 into the tuft hole 125 and then into the bristle tuft 141, as described herein below.

Due to the sloping shape of the floor 126 of the tuft hole 125 relative to the sidewall 191 of the tuft hole 125, a gap 194 exists between the floor 126 of the tuft hole 125 and the bottom end 144 of the bristle tuft 141 located within the tuft hole 125. The gap 194 is an air gap, or an empty space, between the floor 126 of the tuft hole 125 and the bottom end 144 of the bristle tuft 141. This gap 194 facilitates the capillary flow of the first fluid 103 from the reservoir 115 (or from a capillary member 150, described below) into the bottom end 144 of the bristle tuft 141 so that the fluid can wick upwardly within the spaces between the bristle filaments 142 of the bristle tuft 141 as described herein.

Referring to FIGS. 3, 4A, and 4F, in the exemplified embodiment the personal care implement 100 also comprises a capillary member 150 fluidly coupled to the store of the first fluid 103 in the reservoir 115 and to at least one of the plurality of bristle tufts 141. In the exemplified embodiment, the capillary member 150 extends from a first end 151 that is located within the reservoir 115, and preferably at a bottom end of the reservoir 115, to a second end 152 that is located within the second portion 197 of the cavity 114 in the head 120. Thus, the capillary member 150 extends through the reservoir 115, through the remainder of the cavity 114 in the handle 110, and into the second portion 197 of the cavity 114 in the head 120. The second end 152 of the capillary member 150 may abut against an end wall of the second portion 197 of the cavity 114, or it may be spaced from the end wall of the second portion 197 of the cavity 114. In embodiments whereby the second portion 197 of the cavity 114 forms the reservoir, the capillary member 150 may be located only within the second portion 197 of the cavity 114. It is mainly important that the capillary member 150 be fluidly coupled to the store of the fluid 103 in the reservoir 115 (regardless of where exactly the reservoir 115 is located within the body 101) and fluidly coupled to at least one of the bristle tufts 141. In some embodiments, fluid coupling to the at least one of the bristle tufts 141 requires direct physical contact between a portion of the capillary member 150 and a portion of the at least one of the bristle tufts 141, as illustrated in FIG. 4F and described in greater detail below. Specifically, a portion of the capillary member 150 may in some embodiments be in continuous direct physical contact with a bottom end of the bristle tufts 141.

In the exemplified embodiment, the capillary member 150 is an elongated structure formed from a fibrous wicking material. Thus, in some embodiments the capillary member 150 may be referred to as a fibrous wicking member or a fibrous wicking rod or a fibrous wicking pad. Such a fibrous wicking material may be a porous material, a fibrous material, a foam material, a sponge material, natural fibers, sintered porous materials, porous or fibrous polymers or other materials which conduct the capillary flow of liquids through the material itself (such as non-porous materials such as sand and liquefied carbon fiber). Of course, the capillary material of the capillary member 150 is not to be limited by the specific materials noted herein, but can be any material that facilitates movement of a liquid therethrough via capillary action. Furthermore, although described herein as being formed of a fibrous wicking material, the invention is not to be so limited in all embodiments. In certain other embodiments, an example of which will be described below with reference to FIGS. 6A-6C, the capillary member 150 or portions thereof may be formed of a plastic material, a metal material, a wood material, or a rubber material and may have an orifice formed therethrough to enable the first fluid 103 to flow through the capillary member 150 for application to a user's oral cavity.

In the exemplified embodiment, the reservoir 115 is located in the handle 110 and the first fluid 103 is delivered or otherwise transported from the reservoir 115 to the cleaning elements 140 via the capillary member 150. However, the invention is not to be so limited. In other embodiments, the reservoir 115 may be located in the head 120. Thus, for example, the second portion 197 of the cavity 114 may form the reservoir 115, and the cavity 114 in the handle 110 may be omitted in its entirety or it may be left as an empty volume of space. In such an embodiment, the capillary member 150 may still be located within the second portion 197 of the cavity 114 and it may be loaded with the first fluid 103. In other embodiments, the capillary member 150 may be omitted and the first fluid 103 may merely be free-flowing within the second portion 197 of the cavity 114 in the head 120 for dispensing to the cleaning elements 140. In some embodiments, the bottom ends 144 of the bristle tufts 141 may be fluidly coupled to the reservoir 115 directly, rather than indirectly via the capillary member 150. Thus, in some embodiments the first fluid 103 may be free-flowing within the reservoir 115 and from the reservoir 115 to the bristle tufts 141 and in other embodiments the first fluid 103 may flow from the reservoir 115 to the bristle tufts 141 within or along the capillary member 150. Furthermore, it should be appreciated that the reservoir 115, although depicted in the drawings as being located in the handle 110, could also be located entirely or partially within the head 120.

In some embodiments, it may be important for the capillary member 150 to be positioned within the second portion 197 of the cavity 114 in a tight interference fit. Thus, there should not be any gaps or spaces between an outer surface of the capillary member 150 and the walls/surfaces of the body 101 that define the second portion 197 of the cavity 114. However, it should also be ensured that the capillary member 150 is not overly compressed within the second portion 197 of the cavity 114. Thus, there should be a balance between the need for a tight interference fit between the second portion 197 of the cavity 114 and the capillary member 150 and the need to not overly compress the capillary member 150 within the channel. In some embodiments, the second portion 197 of the cavity 114 may have a width W1 measured in a direction between the front and rear surfaces 121, 122 of the head 120 and the capillary member 150 may have a diameter D1. A ratio of the diameter D1 of the capillary member 150 to the width W1 of the second portion 197 of the cavity 114 should be in a range of 1:1 to 1.2:1, more specifically 1:1 to 1.1:1, and still more specifically 1.03:1 to 1.1:1. Thus, the diameter D1 of the capillary member 150 may in some embodiments be only very slightly larger than the width W1 of the second portion 197 of the cavity 114 to achieve the required balance.

Referring to FIGS. 4A and 4F, the personal care implement 100 also comprises a plurality of thru-holes 127. Each of the thru-holes 127 extends from a first opening 128 located in the floor 126 of one of the tuft holes 125 to a second opening 129 that is located in a roof 131 of the second portion 197 of the cavity 114 (the roof 131 of the second portion 197 of the cavity 114 being a wall that defines the second portion 197 of the cavity 114 and is located closest to the floor 126 of the tuft holes 125). In the exemplified embodiment, the first opening 128 is located at or along the apex 192 of the floor 127 of the tuft hole 125. However, the invention is not to be so limited in all embodiments and the first opening 128 could be positioned at other locations along the floor 127. In still other embodiments, the first opening 128 could be located along the sidewall 191 of the tuft hole 125 rather than in the floor 127 of the tuft hole 125.

Each of the thru-holes 127 provides a passageway from the second portion 197 of the cavity 114 to one of the tuft holes 125. Furthermore, the portion of the capillary member 150 that is located within the second portion 197 of the cavity 114 covers, or at least partially covers, the second openings 129 of each of the thru-holes 127. As mentioned above, in the exemplified embodiment the capillary member 150 is formed from a fibrous wicking material. The capillary member 150 comprises a main body 158 having an outer surface 159 and a plurality of fibers 153 that stick out, extend, or otherwise protrude from the outer surface 159 of the main body 158.

At least some of the fibers 153 that protrude from the outer surface 159 of the main body 158 of the capillary member 150 penetrate into and through the thru-holes 127. These fibers 153 of the capillary member 150 extend entirely through the thru-holes 127 and come into direct surface contact with the bottom ends 144 of the bristle tufts 141 located in the tuft holes 125 that are aligned with the thru-holes 127. As a result, the capillary member 150 is fluidly coupled to the fluid 103 in the reservoir 103 and the capillary member 150, via the fibers 153 that extend through the thru-holes 127, is in continuous direct physical contact (or surface contact) with the bristle tufts 141. The fibers 153 of the capillary member 150 penetrating through the thru-holes 127 to contact the bristle tufts 141 directly allows for fluids located within the capillary member 150 to flow from the capillary member 150, through the thru-holes 127 to the bristle tufts 141, and then upwardly along bristle tufts 141, all via capillary action. In some embodiments, the fibers 153 are in continuous physical contact with the bottom ends 144 of the bristle tufts 141. In some embodiments the main body 158 of the capillary member 150 may form a first portion of the capillary member 150 and the fibers 153 extending through the thru-holes 127 may form a second portion of the capillary member 150.

In the exemplified embodiment, there are two of the thru-holes 127 illustrated leading to two different tuft holes 125. However, in other embodiments there may be any number of thru-holes 127 as may be desired. Thus, there may be just a single through-hole 127 extending between the second portion 197 of the cavity 114 and one of the tuft holes 125. In other embodiments, there may be a thru-hole 127 extending between the second portion 197 of the cavity 114 and every one of the tuft holes 125. In other embodiments, there may be a thru-hole 127 extending between the second portion 197 of the cavity 114 and a subset of the tuft holes 125, which could include the tuft holes 125 located along a distal region of the head 120, the tuft holes 125 located along a central region of the head 120, the tuft holes 125 located along a proximal region of the head 120, the tuft holes 125 located along a perimeter region of the head 120, or any desired grouping of tuft holes 125. For each tuft hole 125 that has a thru-hole 127 associated with it, the first fluid 103 will flow, passively via capillary action/wicking, into and upwardly along the bristle tuft 141 that is positioned within the tuft hole 125, as described in greater detail below. Thus, the placement of the thru-holes 127 allows for the targeting of specific bristle tufts 141 to receive the fluid 103 rather than having the fluid 103 flow to all of the bristle tufts 141 (although this is also possible in some embodiments).

In some embodiments, the thru-holes 127 may have a diameter of between 0.1 mm and 0.5 mm, more specifically between 0.2 mm and 0.4 mm, and still more specifically approximately 0.3 mm (approximately including a tolerance, which could be an increase or a decrease, of up to 5%). In the exemplified embodiment, the bottom end 144 of the bristle tuft 141 has a greater diameter than the diameter of the thru-hole 127. Thus, the bottom end 144 of the bristle tuft 141 may be said to surround the thru-hole 127 and the first opening 128 thereof, despite the fact that there may be a gap 193 between the bottom end 144 of the bristle tuft 141 and the first opening 128 of the thru-hole 127.

Referring to FIG. 3 in conjunction with FIGS. 4A-4D sequentially, movement of the first fluid 103 from the reservoir 115 to the bristle tufts 142 will be described. As noted above, a portion of the capillary member 150 that includes the first end 151 is located in the reservoir 115 in contact with the first fluid 103. Due to the capillary member 150 being formed of a capillary material or a fibrous wicking material as described above, the first fluid 103 flows upwardly along the capillary member 150 from the first end 151 to the second end 152 via passive flow or capillary action. Specifically, the first fluid 103 wicks upwardly along the material of the capillary member 150. FIG. 4A illustrates the first fluid 103 extending partway up the capillary member 150. FIG. 4B illustrates the first fluid 103 extending along the entirety of the capillary member 150 all the way to the second end 152 of the capillary member 150. FIG. 4C illustrates the first fluid 103 flowing from the capillary member 150, through the thru-holes 127 (via the fibers 153, although they are not shown in FIG. 4C because it would detract from the overall clarity of the drawings), into the tuft holes 125 from which the thru-holes 127 extend, and into the bottom ends 144 of the bristle tufts 141 that are located within the specific tuft holes 125 that have a thru-hole 127 extending therefrom. Furthermore, as shown in FIG. 4C, the first fluid 103 also begins to wick upwardly along the bristle tufts 141 within the spaces between the bristle filaments 142 of the bristle tufts 141. As the fluid 103 flows towards the bristle tufts 141, air may enter the reservoir 115 via the air vent 132 to maintain pressure in the reservoir 115. As mentioned above, the fluid 103 flows through the thru-holes 127 to the bristle tufts 141 via the fibers 153 of the capillary member 150 that extend through the thru-holes 127 and physically contact the bristle tufts 141.

Thus, the first fluid 103 only flows into the bristle tufts 141 that are associated with one of the thru-holes 127. A bristle tuft 141 is associated with a thru-hole 127 if that bristle tuft 141 is positioned in a tuft hole 125 that has one of the thru-holes 127 extending therefrom. Sated another way, a bristle tuft 141 is associated with a thru-hole 127 if that bristle tuft 141 is positioned in a tuft hole 125 having an opening 128 of one of the thru-holes 127 in its floor 126 or elsewhere along the tuft hole 125. As seen in FIG. 4C, there are only two of the thru-holes 127 fluidly coupling two of the tuft holes 125 to the capillary member 150. Thus, the first fluid 103 only flows from the capillary member 150 into the two tuft holes 127 that are connected to the capillary member 150 via one of the thru-holes 127. The first fluid 103 does not flow into the other bristle tufts 141 because the other bristle tufts 141 are not fluidly coupled to the capillary member 150. Thus, as mentioned previously, in some embodiments a first subset (or at least one) of the bristle tufts 141 is fluidly coupled to the capillary member 150 and a second subset (or at least one) of the bristle tufts 141 is not fluidly coupled to (i.e., are fluidly isolated from) the capillary member 150. In some embodiments, the second subset of the bristle tufts 141 are not fluidly coupled to any reservoir or any fluid such that the second subset of the bristle tufts are free of any liquid (other than liquids that may be placed onto the bristle tufts from external sources, such as a faucet or the like). Of course, all of the bristle tufts 141 may be fluidly coupled to the capillary member 150 in other embodiments. The first fluid 103 only flows into those bristle tufts 141 that are fluidly coupled to the capillary member 150. In this manner, the location of the first fluid 103 within the bristle field as well as the dosage thereof during use of the personal care implement 100 can be controlled.

Referring to FIGS. 4D and 4E, the first fluid 103 continues to wick upwardly along the bristle tufts 141 that are fluidly coupled to the capillary member 150 via capillary action. Again, no action is taken by the user to cause this flow of the first fluid 103 into the bristle tufts 141 and upwardly along the bristle tufts 141. Rather, this flow of the first fluid 103 occurs entirely naturally and passively. The first fluid 103 may wick upwardly along the bristle tufts 141 that are fluidly coupled to the capillary member 150 until the first fluid 103 reaches the distal ends 143 of those bristle tufts 141. Of course, depending on the dimensions of the spaces between the bristle filaments 142, the first fluid 103 may not wick all the way to the distal ends 143. Specifically, the larger the dimensions of the spaces between the bristle filaments 142, the less likely it is that the first fluid 103 will wick upwardly along the bristle tufts 141. The fluid 103 wicks upwardly along the bristle tufts 141 within the spaces between the bristle filaments 142 due to a combination of surface tension which is caused by cohesion within the fluid 103 and adhesive forces between the fluid 103 and the outer surface of the bristle filaments 142.

FIG. 4E is a close-up cross-sectional view of one of the bristle tufts 141 that is fluidly coupled to the capillary member 150. In this figure, the spaces 149 between the bristle filaments 142 within the bristle tuft 141 are visible. As discussed thoroughly above, the first fluid 103 wicks upwardly along the bristle tuft 141 within the spaces 149 between the bristle filaments 142 naturally via capillary action.

Figure 5A:
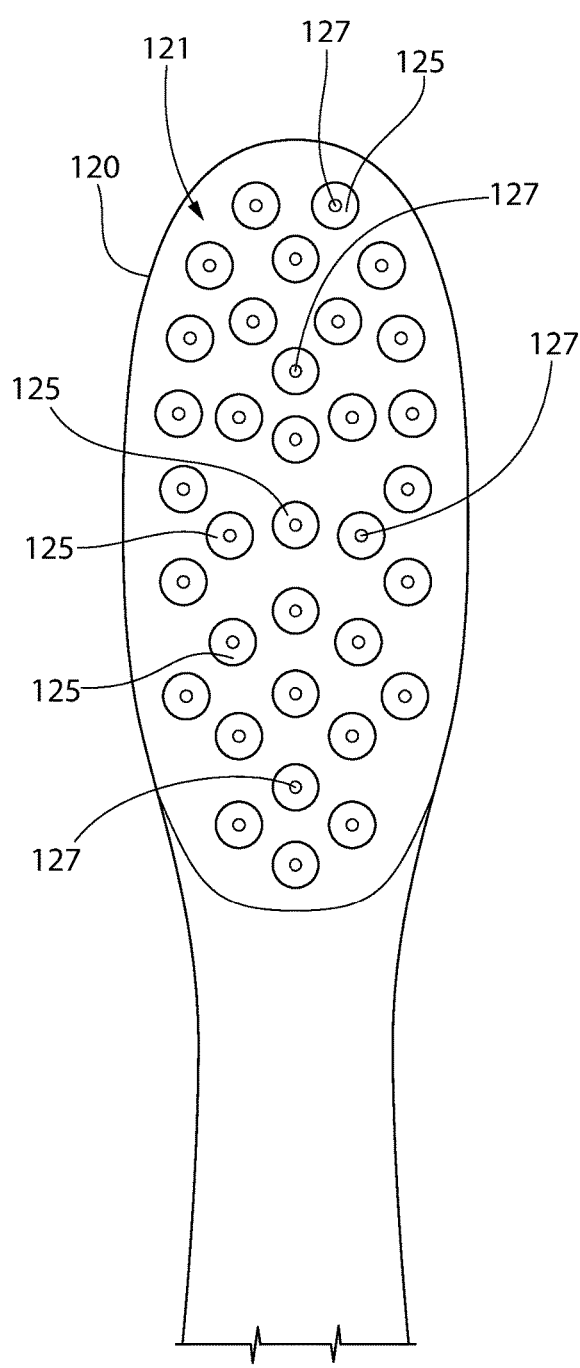
FIG. 5A is a front view of a head of the personal care implement of FIG. 1 with the cleaning elements omitted in accordance with a first embodiment of the present invention.
Figure 5B:
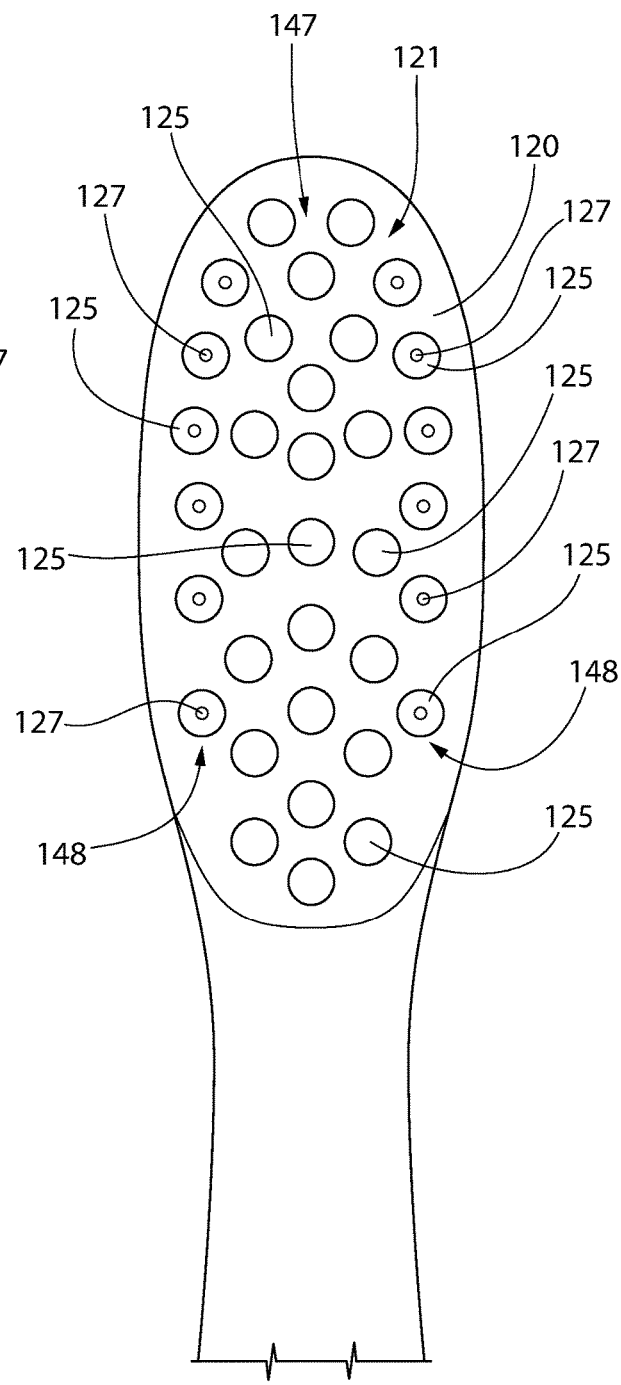
FIG. 5B is a front view of a head of the personal care implement of FIG. 1 with the cleaning elements omitted in accordance with a second embodiment of the present invention.

As mentioned above, in the exemplified embodiment not all of the bristle tufts 142 are fluidly coupled to the capillary member 150. This is because not all of the tuft holes 125 have a thru-hole 127 extending from the floor 126 of that tuft hole 125 to the capillary member 150. Without being positioned in a tuft hole 125 having a thru-hole 127 therein, a bristle tuft 141 has no way of being fluidly coupled to the capillary member 150. FIGS. 5A and 5B illustrate two alternative embodiments depicting a front view of the head 120 without any bristle tufts 141 coupled to the head 120. In FIG. 5A, there is a thru-hole 127 extending from every single one of the tuft holes 126 to the capillary member 150 (or to the second portion 197 of the cavity 114 within which the capillary member 150 is positioned). Differently, in FIG. 5B there is a thru-hole 127 extending from a subset of the tuft holes 126 to the capillary member 150. Specifically, in FIG. 5B there are only thru-holes 127 extending from the tuft holes 126 located along the perimeter of the front surface 121 of the head 120. Thus, in FIG. 5B the bristle tufts that are ultimately located within the tuft holes 125 located along the perimeter of the front surface 121 of the head 120 make up the subset of bristle tufts 141 that are coupled to the capillary member 150. In FIG. 5B a first subset 148 of the bristle tufts 141 (i.e., the ones located in the tuft holes 125 that have thru-holes 127 therein) would be fluidly coupled to the capillary member 150 and a second subset 147 of the bristle tufts 141 (i.e., the ones in the tuft holes 125 that do not have thru-holes therein) would be not fluidly coupled to the capillary member 150.

FIGS. 14A-14D illustrate this concept from an overhead or top view of the head 120. Specifically, in FIGS. 14A-14D, the bristle tufts 141 that are shown in grayscale are fluidly coupled to the fluid in the reservoir 115 and the bristle tufts 141 that are white are fluidly isolated from the fluid in the reservoir 115 (i.e., not fluidly coupled to the reservoir 115). Thus, the bristle tufts 141 that are shown in grayscale form a part of the first subset 148 of the bristle tufts 141 and the bristle tufts 141 that are white form a part of the second subset 147 of the bristle tufts 141.

Figure 14A:
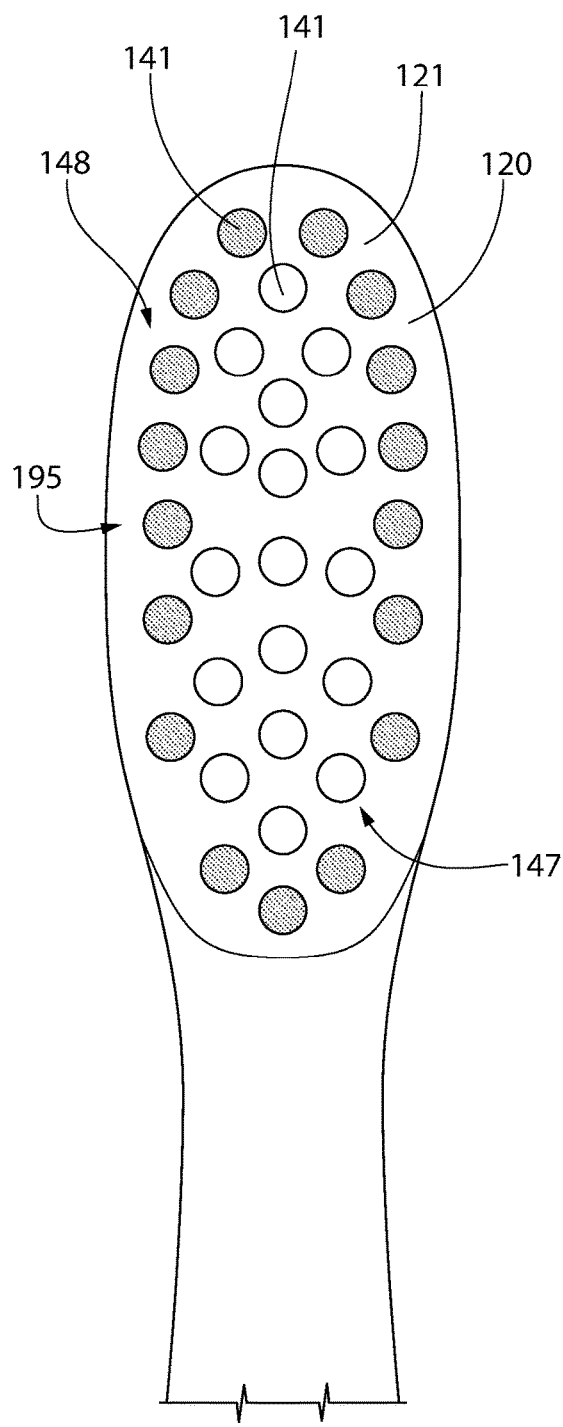
FIGS. 14A-14D are schematic illustrations depicting subsets of bristle tufts that are fluidly coupled to and fluidly isolated from a fluid reservoir.
Figure 14B:
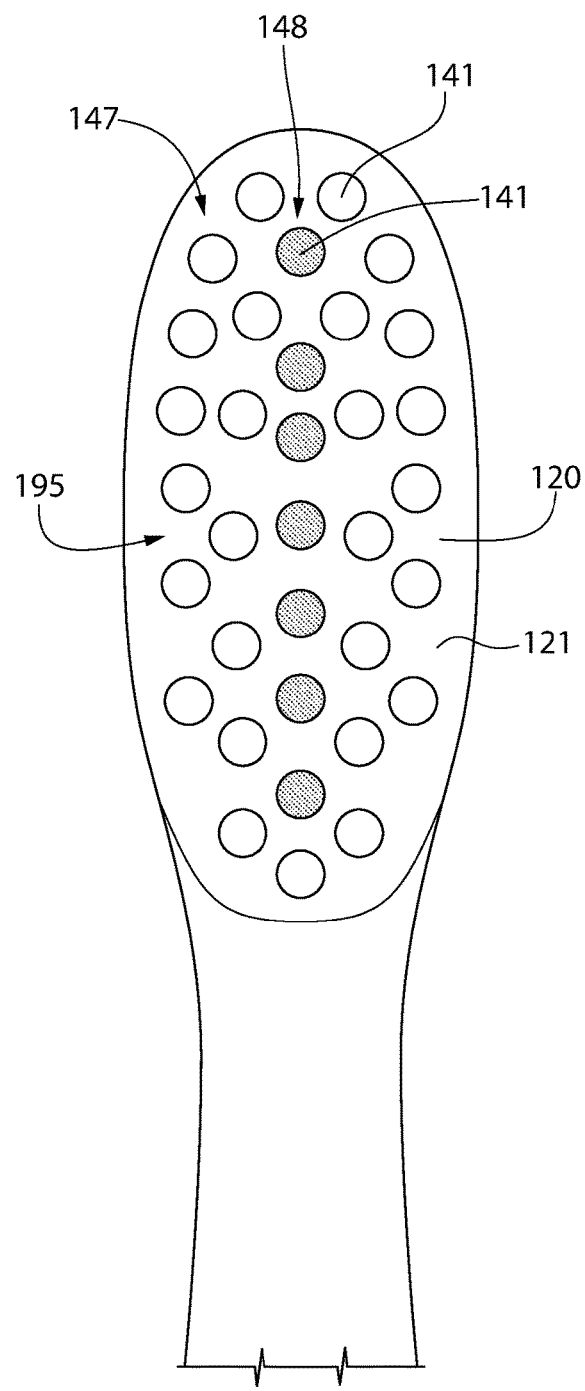
Figure 14C:
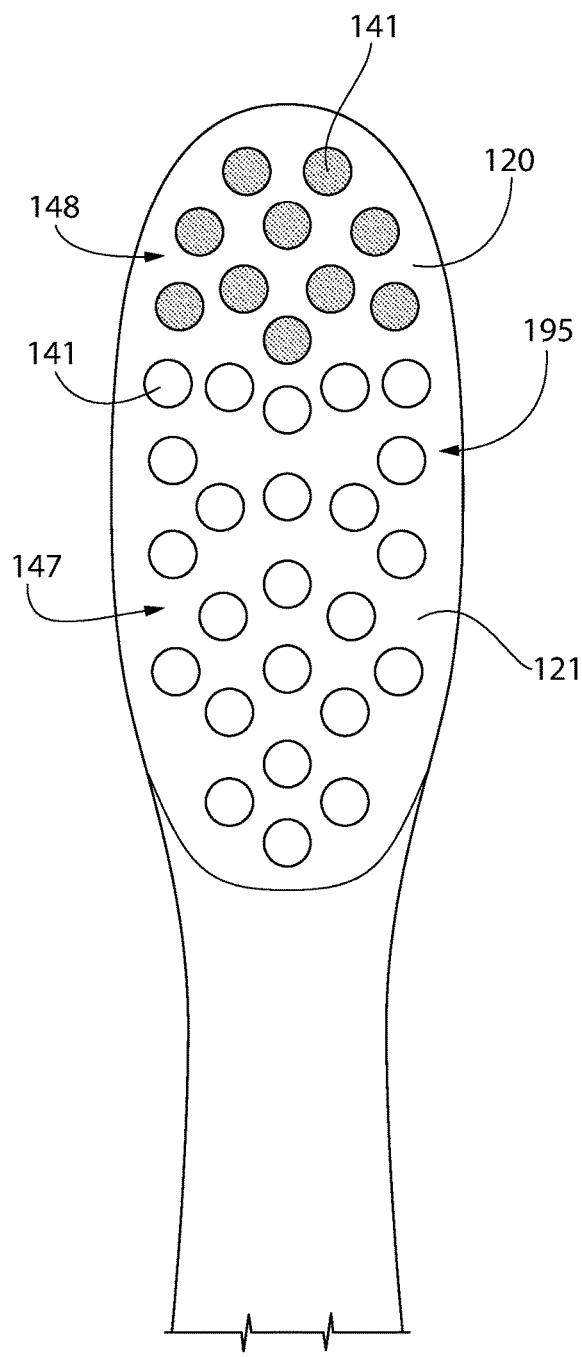
Figure 14D:
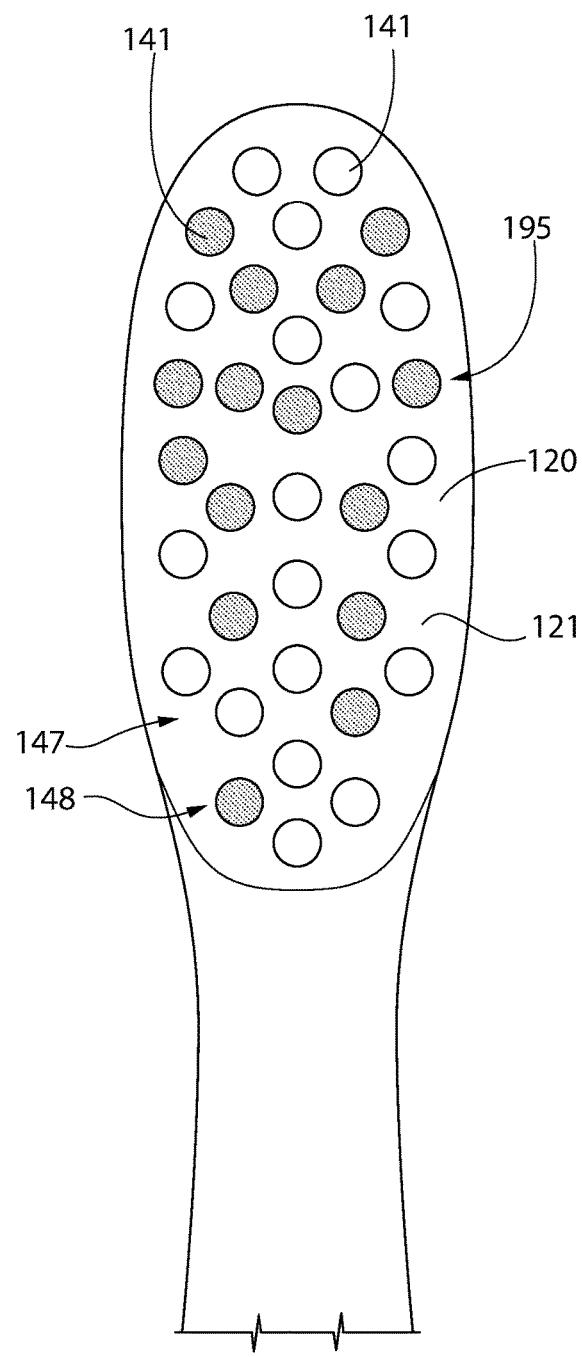

Referring to FIGS. 14A-14D, the bristle tufts 141 collectively form a bristle field 195. In FIG. 14A, the first subset 148 of the bristle tufts 141 are arranged along a perimeter or periphery of the bristle field 195 and the second subset 147 of the bristle tufts 141 are located along a center region of the bristle field 195. Thus, in this embodiment the first subset 148 of the bristle tufts 141 surrounds the second subset 147 of the bristle tufts 141. In FIG. 14B, the first subset 148 of the bristle tufts 141 are located along a center portion of the bristle field 195 and are aligned with the longitudinal axis of the head 120. Furthermore, the second subset 147 of the bristle tufts 141 surround the first subset 148 of the bristle tufts 141 in this embodiment. In FIG. 14C, the first subset 148 of the bristle tufts 141 are located along a distal portion of the bristle field 195 with the rest of the bristle tufts 141 forming a part of the second subset 147 of the bristle tufts 141. Finally, FIG. 14D illustrates an arrangement whereby a random selection of the bristle tufts 141 form a part of the first subset 148 that are fluidly coupled to the fluid in the reservoir and a random selection of the bristle tufts 141 form a part of the second subset 147 that are fluidly isolated from the fluid in the reservoir. In some embodiments, all of the bristle tufts 141 of the second subset 147 are fluidly isolated from any fluid, and therefore no fluid at all flows to those bristle tufts 141 from an interior location within the personal care implement.

Of course, the specific ones of the tuft holes 125 that are fluidly coupled to the capillary member 150 (or the second portion 197 of the cavity 114) via these thru-holes 127 can be modified as desired (at the time of manufacturing the personal care implement 100) to select the bristle tufts 141 that will have the first fluid 103 delivered to them passively by capillary action. Specifically, during manufacture of the personal care implement 100, the thru-holes 127 can be formed in a desired arrangement so that the first fluid 103 wicks upwardly along the bristle tufts 141 in a particular location on the head 120. This could include only having thru-holes 127 in the tuft holes 125 located along the distal portion of the head 120, the proximal portion of the head 120, the central portion of the head 120, the peripheral sides of the head 120, or the like. Not all of these possibilities are illustrated in the drawings because there are infinite different ways that this could be done. Nonetheless, the concept should be readily apparent to those persons skilled in the art and certain benefits may be achieved by selecting a desired location or portion of the bristle field 195 for the fluid to flow to.

Moreover, determining which of the bristle tufts 141 (or tuft holes 125) to fluidly couple to the capillary member 150 may also be done to achieve supplying a desired dose of the first fluid 103 during use of the personal care implement 100. For example, a manufacturer may be able to determine the amount of the first fluid 103 that can be held in each of the bristle tufts 141 when saturated. The manufacturer could then select a specific subset of the bristle tufts 141 to be fluidly coupled to the capillary member 150 based on the location of the thru-holes 127 to ensure that the total amount of the first fluid 103 that is held in all of the bristle tufts 141 that are fluidly coupled to the capillary member 150 when saturated equals a desired, pre-determined dose of the first fluid 103.

In certain embodiments, the capillarity of the capillary member 150 and the bristle tufts 141 should be configured to ensure that the fluid 103 can flow passively from the capillary member 150 to the bristle tufts 141. Specifically, it is known that fluids 103 flow from lower capillarity materials to higher capillarity materials, but not vice versa. Thus, if the bristle tufts 141 have a lower capillarity than the capillary member 150, the fluid 103 may not flow passively from the capillary member 150 to the bristle tufts 141. Thus, in some embodiments the capillary member 150 has a first capillarity and the bristle tufts 141 that are fluidly coupled to the capillary member 150 have a second capillarity such that the first capillarity is lower than the second capillarity.

Figures 6A, 6B:
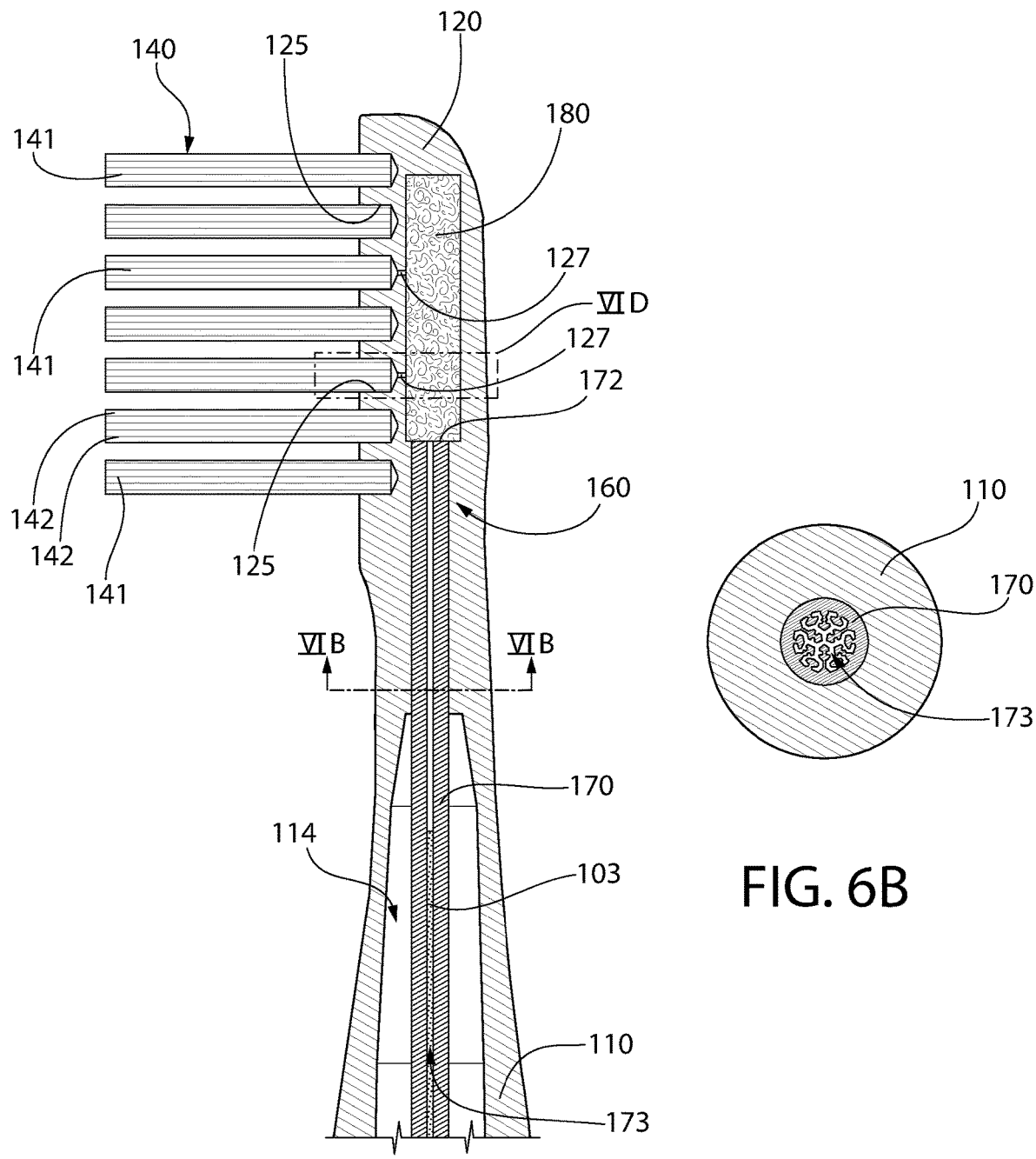
FIG. 6A is a close-up view of area IV of FIG. 3 in accordance with an alternative embodiment of the present invention, whereby a capillary member includes a capillary tube and a capillary pad.
FIG. 6B is a cross-sectional view taken along line VIB-VIB of FIG. 6A.

Referring to FIGS. 6A and 6B, an alternative embodiment of a capillary member 160 will be described. In this embodiment, the capillary member 160 comprises a capillary tube 170 and a capillary pad 180. The capillary tube 170 extends from a first end (not shown in these views, but similar to the first end 151 of the capillary member 150 shown in FIG. 3) that is located within the reservoir 115 and fluidly coupled to the first fluid 103 located in the reservoir 115 to a second end 172 that is fluidly coupled to the capillary pad 180. The capillary pad 180 is located within the second portion 197 of the cavity 114 of the head 120 beneath the cleaning elements 140 at a location that is aligned with the thru-holes 127 so that the capillary pad 180 covers each of the thru-holes 127. Thus, the capillary tube 170 transports the first fluid 103 from the reservoir 115 to the capillary pad 180, as described herein. Of course, in some embodiments the capillary pad 180 may be pre-loaded with the store of the fluid 103 and thus the capillary tube 170 may be omitted. In the exemplified embodiment, the capillary pad 180 is entirely housed within the body 101 of the personal care implement 100 such that no portion of the capillary pad 180 is exposed. Thus, the capillary pad 180 does not make direct contact with a user during use of the personal care implement 100 but merely transports/delivers the first fluid to the bristle tufts 141 as described herein.

In the exemplified embodiment, the capillary tube 170 is formed of a rigid material (e.g., plastic, rubber, metal, wood, or the like) and has a capillary passageway 173 extending entirely through the capillary tube 170 from the first end to the second end 172 that permits the first fluid 103 to flow within the capillary tube 170 from the first end to the second end 172 via a wicking action. In this embodiment, the capillary tube 170 may not be formed of a porous material, but rather it may be formed of a non-porous material. However, the capillary passageway 173 has a cross-sectional size and shape that is quite small so that it permits, and in fact forces, the flow of the first fluid 103 all the way from the reservoir 115 to the capillary pad 180. Specifically, because the cross-sectional dimensions of the capillary passageway 173 are so small, once the capillary tube 170 is positioned within the first fluid 103 in the reservoir 115, the first fluid 103 naturally flows upwardly within the capillary passageway 173 towards the second end 172 of the capillary tube 170. One example of the cross-sectional shape of the capillary passageway 173 is illustrated in FIG. 6B. Of course, the invention is not to be limited by the specific shape illustrated, but the shape and dimensions of the capillary passageway 173 are selected to ensure that the first fluid 103 will flow all the way to the second end 172 of the capillary tube 170 without any action being required by the user. This embodiment is not to be limited to the capillary tube 170 being a rigid material with a capillary passageway 173. In other embodiments, the capillary tube 170 may be identical to the capillary member 150 such that it is formed of a fibrous wicking material and in that regard the description of the previous embodiment may be applicable.

Thus, in this manner the first fluid 103 is able to flow from its storage location within the reservoir 115 and through the capillary passageway 173 of the capillary tube 170 to the capillary pad 180 so that the capillary pad 180 can be loaded with the fluid. In that regard, the capillary pad 180 is preferably formed of a fibrous wicking material, such as without limitation a porous material, a fibrous material, a foam material, a sponge material, natural fibers, sintered porous materials, porous or fibrous polymers or other materials which conduct the capillary flow of liquids. As with the earlier described embodiment, the flow of the fluid occurs naturally via capillary action from the reservoir 115 to the capillary pad 180 without the need for a separate pump. The capillary pad 180 may be formed of an identical material as the capillary member 150 described in the previous embodiment.

Figure 6C:
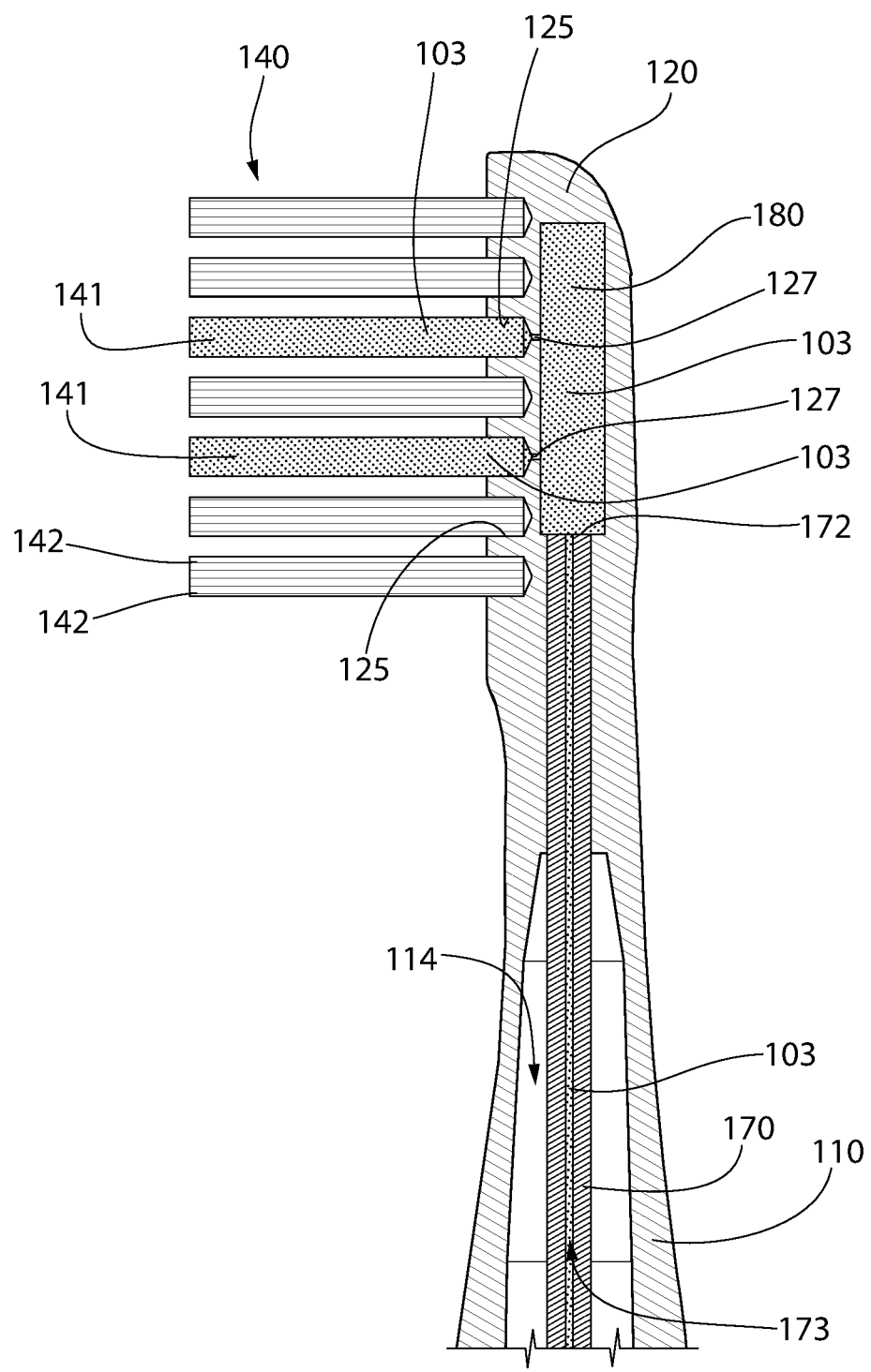
FIG. 6C is the close-up view of FIG. 6A illustrating a fluid being delivered to the bristles.
Figure 6D:
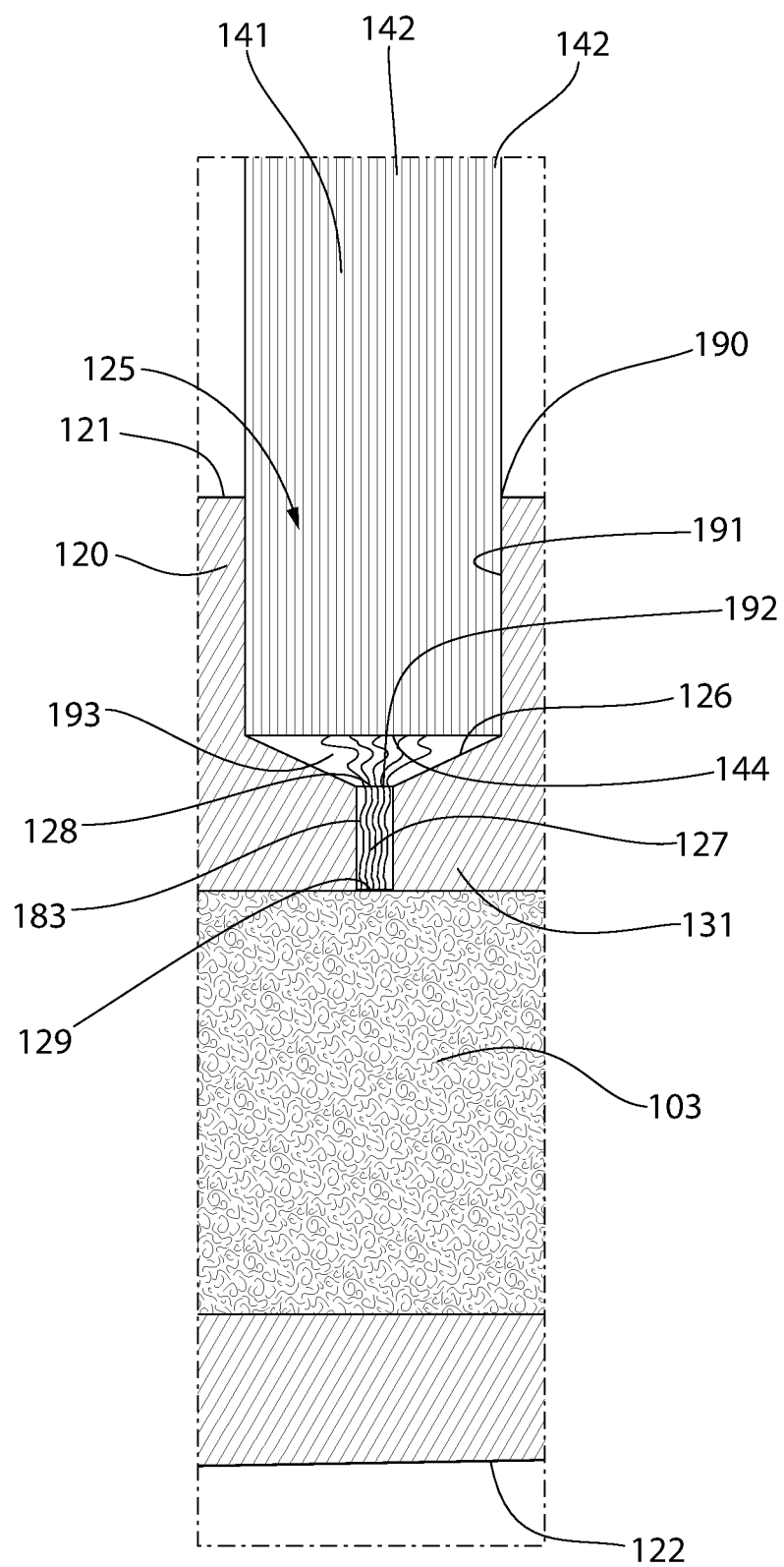
FIG. 6D is a close-up view of area VID of FIG. 6A.

Referring to FIGS. 6C and 6D, once the capillary pad 180 is loaded with the first fluid 103, the first fluid 103 will flow through the thru-holes 127 and into the bristle tufts 141 so that it can wick upwardly within the spaces between the bristle filaments 142 of the bristle tufts 141 in the exact manner as described above. As with the previously described embodiment, the capillary pad 180 may comprise a plurality of fibers 183 that extend through the thru-holes 127 to make direct physical contact with the bristle tufts 141. In some embodiments, the capillary pad 180 may be slightly compressed when it is positioned within the channel in the head 120. Such compression of the capillary pad 180 may help to force the fluid out of the capillary pad 180 and into the bristle tufts 141 via the thru-holes 127. This is akin to squeezing a sponge, which causes fluids loaded on the sponge to separate from the sponge. FIG. 6C illustrates the first fluid 103 having filled the capillary passageway 173 of the capillary tube 170, loaded (and possibly saturated) the capillary pad 180, and passed into the thru-holes 127 (via the fibers 183) and into the bristle tufts 141 that are fluidly coupled to the capillary pad 180. The first fluid 103 flows or wicks upwardly along the bristle tufts 141 within the spaces between the bristle filaments 142 as described above and this all occurs passively via capillary action. A user does not need to squeeze the body 101 to pump the fluid to the bristle tufts 141 because the flow occurs naturally without any action needed by the user.

Figure 7A:
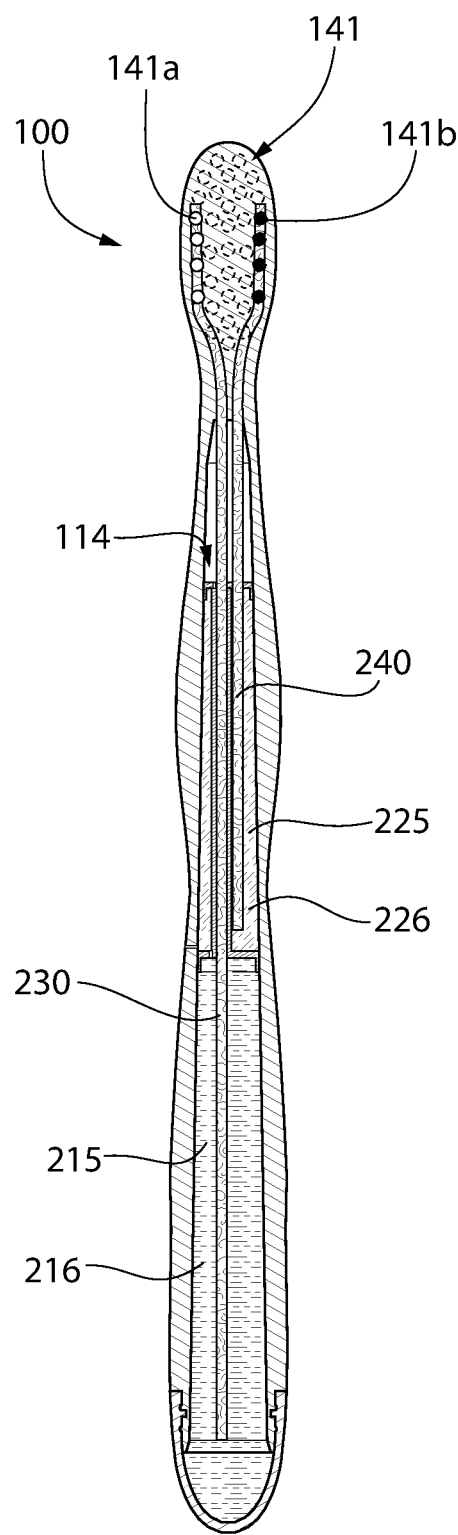
FIG. 7A is a cross-sectional view taken along line VII-VII of FIG. 1 in accordance with a first alternative embodiment of the present invention.
Figure 7B:
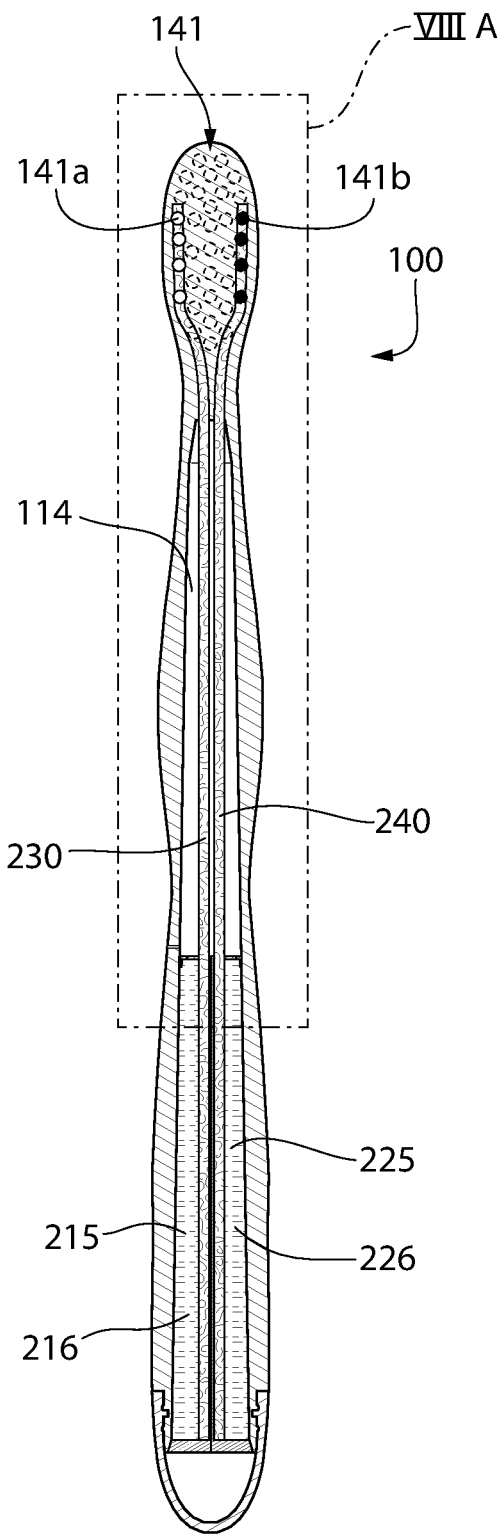
FIG. 7B is a cross-sectional view taken along line VII-VII of FIG. 1 in accordance with a second alternative embodiment of the present invention.

FIGS. 7A and 7B illustrate two different embodiments in accordance with the present invention whereby the personal care implement 100 comprises two reservoirs for holding two different stores of a fluid. First, referring to FIG. 7A, the handle 110 comprises the cavity 114 as previously described. However, in this embodiment a first portion of the cavity 114 forms a first reservoir 215 containing a store of a first fluid 216 and a second portion of the cavity 114 forms a second reservoir 225 containing a store of a second fluid 226. In FIG. 7A, the first and second reservoirs 215, 225 are spaced apart from one another in the direction of the longitudinal axis of the personal care implement 100. Thus, the second reservoir 225 is located above the first reservoir 215. FIG. 7B is identical to FIG. 7A except that the first and second reservoirs 215, 225 are positioned in a side-by-side arrangement.

Thus, the embodiments of FIGS. 7A and 7B illustrate two alternative manners in which the personal care implement 100 could be made with the first and second reservoirs 215, 225. In the exemplified embodiments, the first and second reservoirs 215, 225 are fluidly separated from one another so that the first and second fluids 216, 226 are maintained separate from one another until they are dispensed in accordance with use of the personal care implement 100. Thus, the first and second fluids 216, 226 do not mix with one another within the reservoirs 215, 225 but will only mix once dispensed in accordance with standard use of the personal care implement 100. In certain embodiments, the first and second fluids 216, 226 are different from one another. However, the first and second fluids 216, 226 may provide a benefit when used in conjunction with one another and/or are otherwise mixed at the point of contact with a user's oral cavity or other application surface. In other embodiments, the first and second fluids 216, 226 may simply provide two different therapeutic or other benefits, such as one being a flavor agent and the other being a whitening agent or a sensitivity agent or the like.

Referring to both of FIGS. 7A and 7B, the personal care implement 100 comprises a first capillary member 230 fluidly coupled to the first fluid 216 within the first reservoir 215 and to at least one first bristle tuft 141a of the plurality of bristle tufts 141. In the exemplified embodiment, the first capillary member 230 is fluidly coupled to four of the bristle tufts 141a. However, there could be more or less than four of the bristle tufts 141a fluidly coupled to the first capillary member 230, which is dictated based on the positioning of thru-holes fluidly coupling the bristle tufts 141a to the first capillary member 230, as described above. The first capillary member 230 transports/delivers the first fluid 216 from the first reservoir 215 to each of the first bristle tufts 141a via capillary action as described above.

The personal care implement 100 also comprises a second capillary member 240 fluidly coupled to the second fluid 226 within the second reservoir 225 and to at least a second bristle tuft 141b of the plurality of bristle tufts 141. In the exemplified embodiment, the second capillary member 240 is fluidly coupled to four of the bristle tufts 141b. However, there could be more or less than four of the bristle tufts 141b fluidly coupled to the second capillary member 240, which is dictated based on the positioning of thru-holes fluidly coupling the bristle tufts 141b to the second capillary member 240, as described above. The second capillary member 240 delivers the second fluid 226 from the second reservoir 225 to each of the second bristle tufts 141b via capillary action as described above.

In this embodiment, the first and second capillary members 230, 240 are the same, in terms of material of manufacture, as the capillary member 150. Thus, the first and second capillary members 230, 240 are formed from a fibrous wicking material, such as without limitation, a porous material, a fibrous material, a foam material, a sponge material, natural fibers, sintered porous materials, porous or fibrous polymers or other materials which conduct the capillary flow of liquids. This enables the first and second fluids 216, 226 to flow through the first and second capillary members 230, 240 to a desired subset of the bristle tufts 141 as described herein.

Figure 8A:
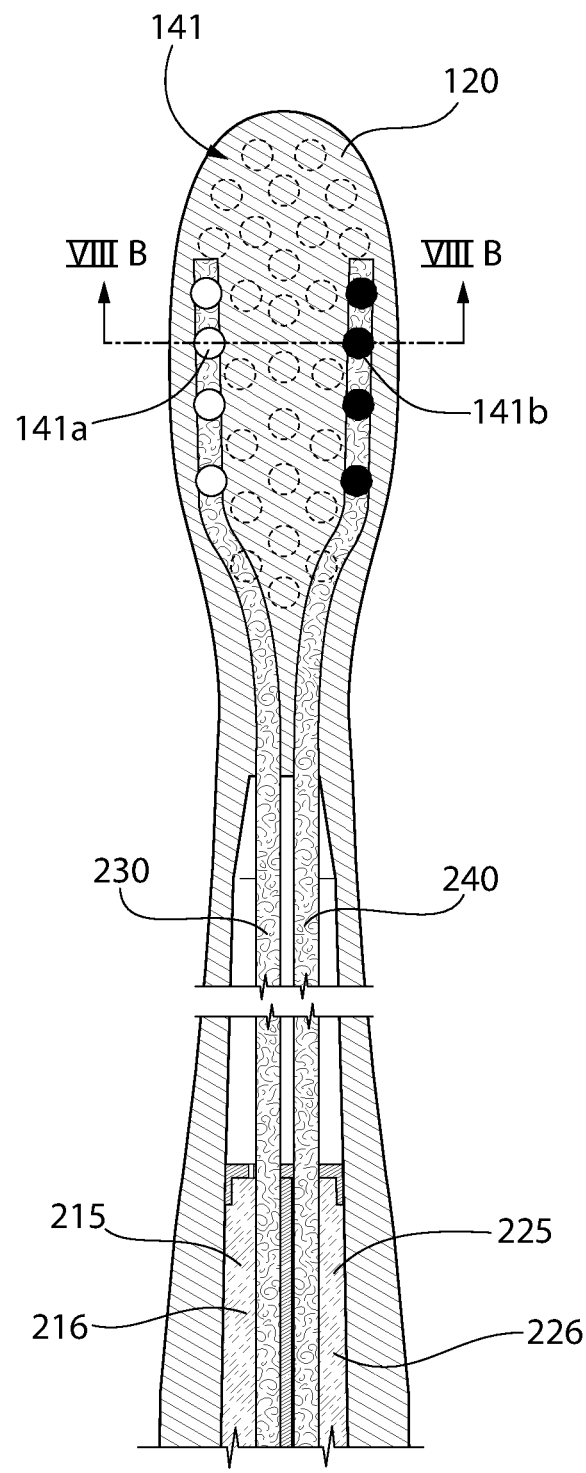
FIG. 8A is a close-up view of area VIIIA of FIG. 7B.
Figure 8B:
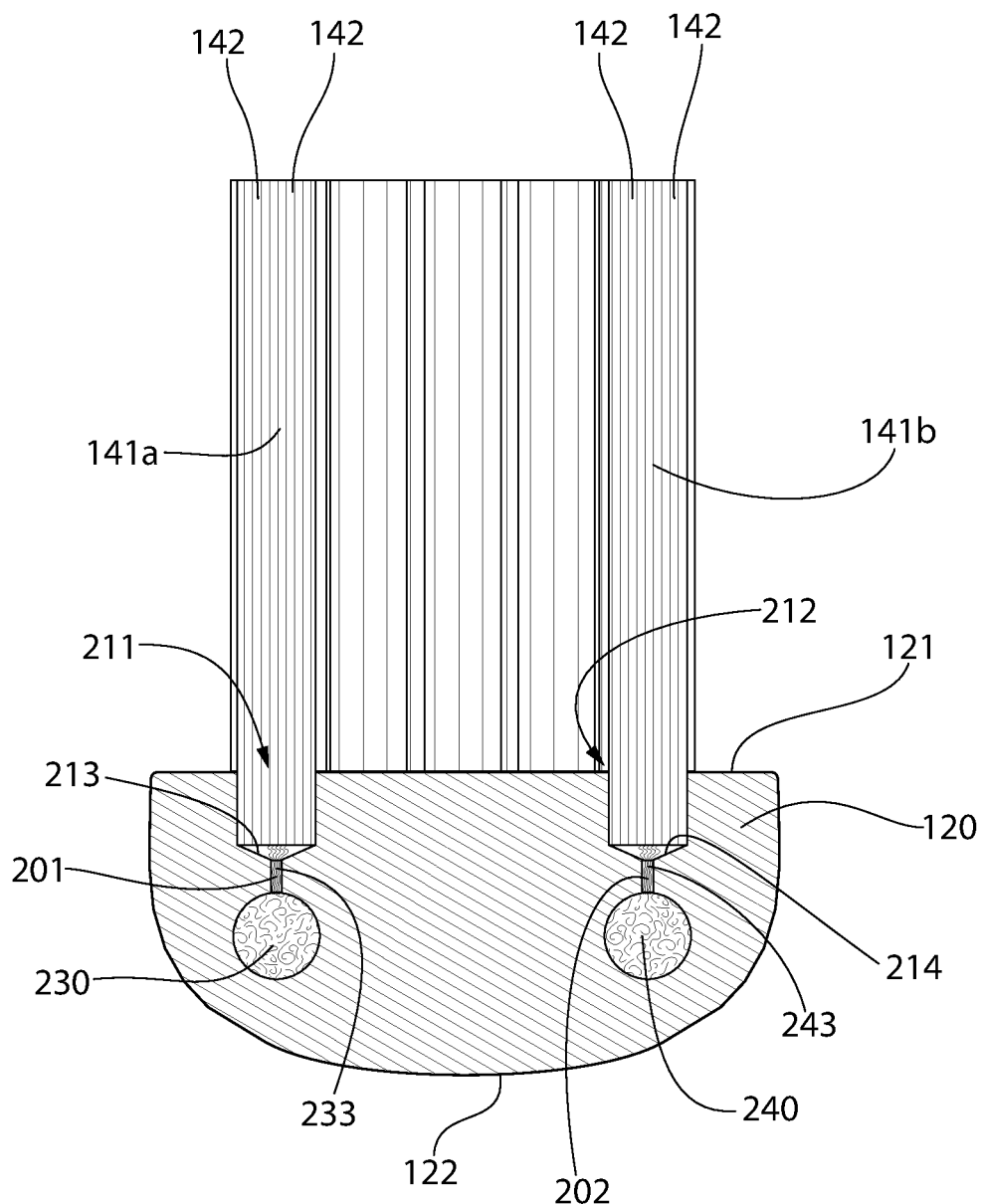
FIG. 8B is a cross-sectional view taken along line VIIIB-VIIIB of FIG. 8A

Referring to FIGS. 8A and 8B concurrently, the dual-reservoir embodiment will be further described with reference to the side-by-side arrangement of FIG. 7B, although it is equally applicable to the above-below arrangement of FIG. 7A. As noted above, the first capillary member 230 is fluidly coupled to at least one first bristle tuft 141a and the second capillary member 240 is fluidly coupled to at least one second bristle tuft 141b. More specifically, the first bristle tuft 141a is positioned within a first tuft hole 211 and the second bristle tuft 141b is positioned within a second tuft hole 212. The first tuft hole 211 has a floor 213 and the second tuft hole 212 has a floor 214. A first thru-hole 201 extends from the floor 213 of the first tuft hole 211 to the first capillary member 230, thereby fluidly coupling the first capillary member 230 to the first bristle tuft 141a. A second thru-hole 202 extends from the floor 214 of the second tuft hole 212 to the second capillary member 240, thereby fluidly coupling the second capillary member 240 to the second bristle tuft 141b. Fibers 233 of the first capillary member 230 extend through each of the thru-holes 201 to make physical contact with the bristle tufts 141a and fibers 243 of the second capillary member 240 extend through each of the thru-holes 202 to make direct physical contact with the bristle tufts 141b.

As shown in FIG. 8A, the first capillary member 230 is fluidly coupled to four of the first bristle tufts 141a (via the fibers 233) and the second capillary member 240 is fluidly coupled to four of the second bristle tufts 141b (via the fibers 243). For each of the bristle tufts 141a that is fluidly coupled to the first capillary member 230, there is a thru-hole 201 extending from the floor 213 of the tuft hole 211 within which the bristle tuft 141a is positioned to the first capillary member 230 and some of the fibers 233 extend into and through the thru-holes 201. Similarly, for each of the bristle tufts 141b that is fluidly coupled to the second capillary member 240, there is a thru-hole 202 extending from the floor 214 of the tuft hole 212 within which the bristle tuft 141b is positioned to the second capillary member 240 and some of the fibers 243 extend into and through the thru-holes 202. This allows the first fluid 216 to flow from the first capillary member 230 to each of the first bristle tufts 141a and allows the second fluid 226 to flow from the second capillary member 240 to each of the second bristle tufts 141*b*. Of course, the exact bristle tufts 141*a*, 141*b* that are fluidly coupled to the first and second capillary members 230, 240 can be modified by adjusting the location of the thru-holes 201, 202. Thus, the first and second bristle tufts 141*a*, 141*b* could be located along the perimeter of the bristle field as shown in FIG. 8A, along a center of the bristle field, along a distal portion of the bristle field, or in any other location as may be desired.

Furthermore, although two reservoirs are depicted in these embodiments, it is possible in other embodiments to have more than two reservoirs. For each reservoir, there should be a capillary member that fluidly couples the reservoir to one or more of the bristle tufts 141 as described herein. Thus, one, two, three, four, or more different fluids can be delivered from a reservoir within the handle 110 to any number of different bristle tufts 141. Furthermore, although in the exemplified embodiment each distinct bristle tuft 141 is only fluidly coupled to one of the first and second fluids 216, 226, it is possible in other embodiments to fluidly couple both of the first and second fluids 216, 226 within the first and second reservoirs 215, 225 to the same bristle tuft 141. For example, there could be two distinct (fluidly separated, not fluidly coupled) thru-holes extending from one of the tuft holes 125 such that one of the thru-holes fluidly couples the bristle tuft 141 within that tuft hole 125 to the first fluid 216 and the other one of the thru-holes fluidly couples the bristle tuft 141 within that tuft hole 125 to the second fluid 226. Thus, two different fluids 216, 226 could be delivered to the same bristle tuft 141 utilizing the techniques and structure described herein.

In some embodiments, it may be possible to adjust or modify whether the various reservoirs 215, 225 are fluidly coupled to any of the bristle tufts 141. Thus, there may be a knob, switch, toggle, button, or other mechanism to facilitate altering the various reservoirs between being fluidly coupled to one or more of the bristle tufts 141 and to not being fluidly would with any of the reservoirs. In some embodiments, it may be possible to alter the fluid couplings so that in some instances both of the first and second reservoirs 215, 225 are fluidly coupled to one or more of the bristle tufts 141, in some instances only one of the first and second reservoirs 215, 225 is fluidly coupled to one or more of the bristle tufts 141, and in some instances neither of the first and second reservoirs 215, 225 is fluidly coupled to any of the bristle tufts 141.

Figure 9A:
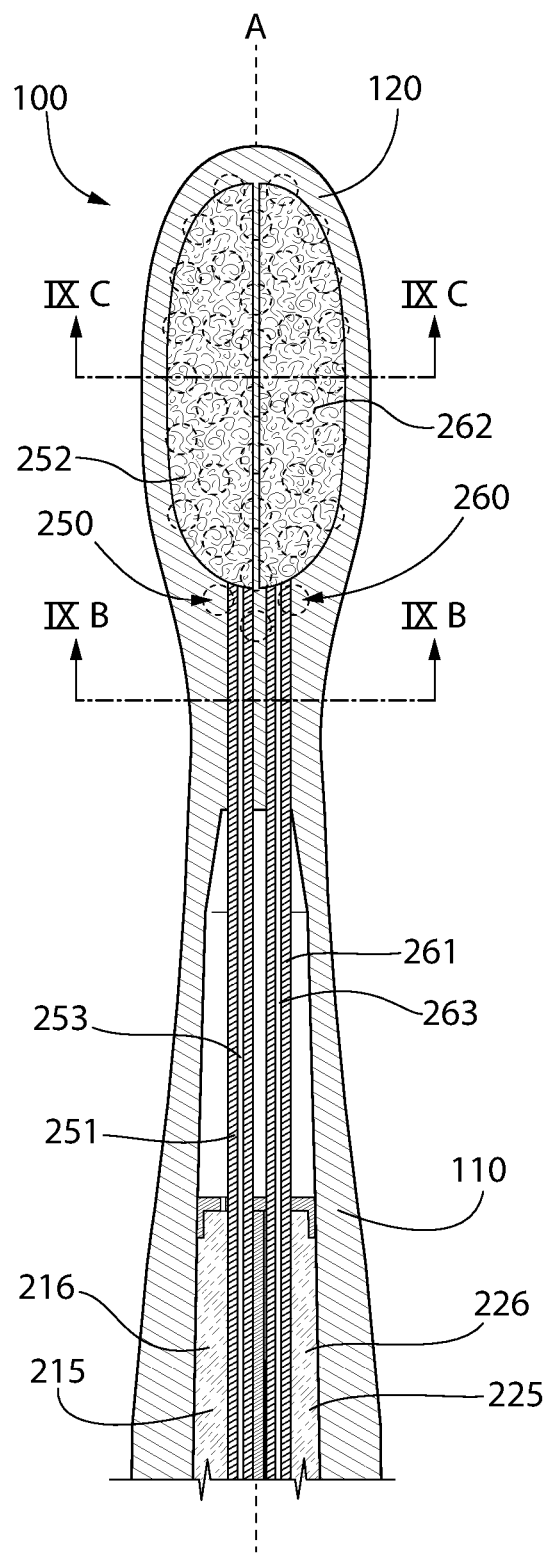
FIG. 9A is a close-up view of area VIIIA of FIG. 7B in accordance with an alternative embodiment of the present invention.
Figure 9B:
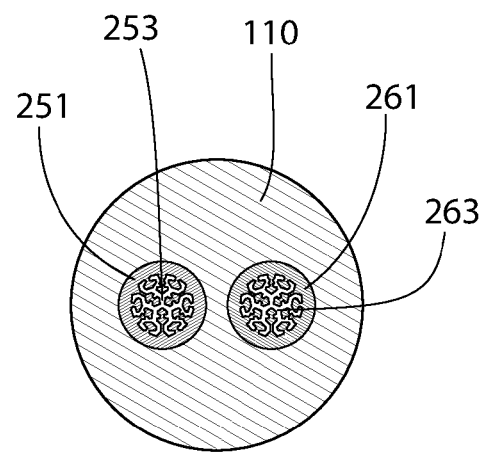
FIG. 9B is a cross-sectional view taken along line IXB-IXB of FIG. 9A.
Figure 9C:
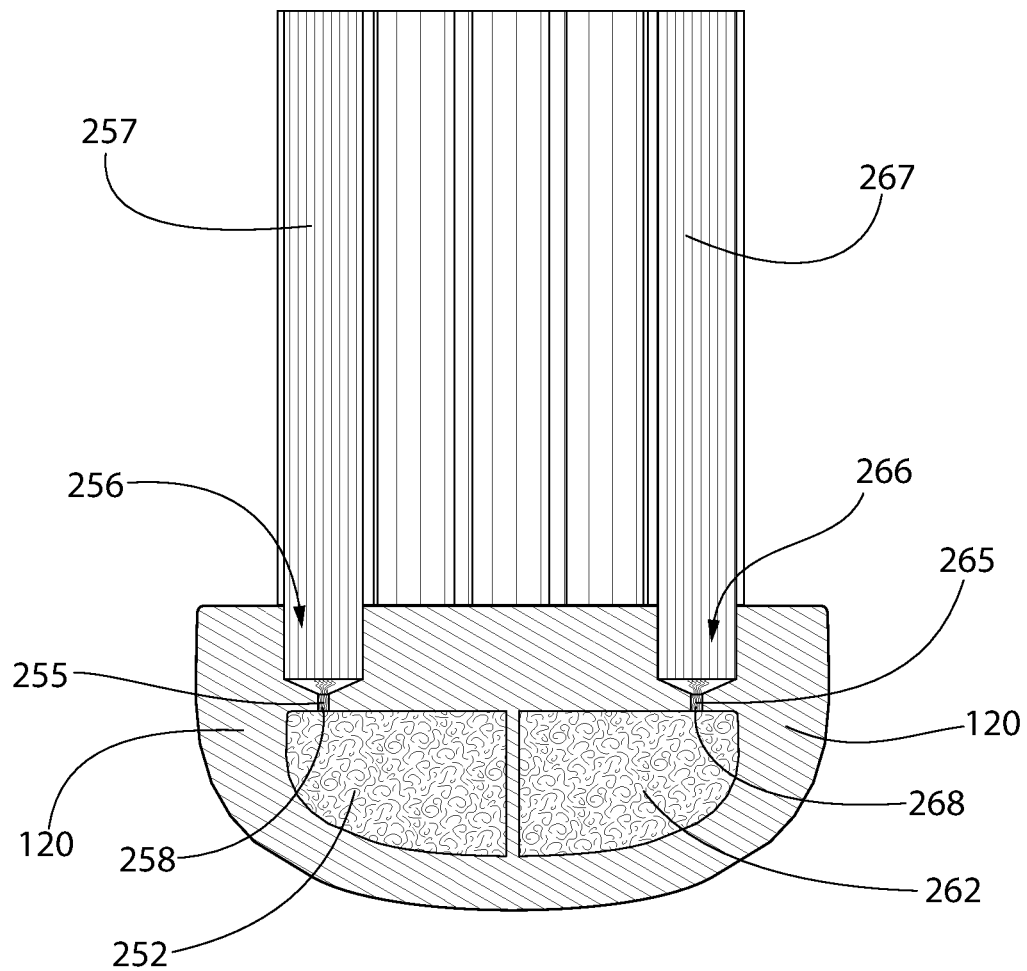
FIG. 9C is a cross-sectional view taken along line IXC-IXC of FIG. 9A.

Referring to FIGS. 9A-9C, an alternative embodiment of the personal care implement 100 having the first and second reservoirs 215, 225 is illustrated. The embodiment of FIGS. 9A-9C is identical to the embodiment of FIGS. 7B, 8A, and 8B except that the structure of the capillary member has been changed to more closely resemble the capillary member 160 of FIGS. 6A and 6B. Specifically, in this embodiment there is a first capillary member 250 comprising a first capillary tube 251 and a first capillary pad 252 and a second capillary member 260 comprising a second capillary tube 261 and a second capillary pad 252. The first capillary tube 251 has a first end that is fluidly coupled to the first fluid 216 in the first reservoir 215 and a second end that is fluidly coupled to the first capillary pad 252. Thus, the first fluid 216 flows, via capillary action, from the first reservoir 215, through the capillary passageway 253 of the first capillary tube 251, to the first capillary pad 252 whereby the first capillary pad 252 becomes loaded with the first fluid 216. The second capillary tube 261 has a first end that is fluidly coupled to the second fluid 226 in the second reservoir 225 and a second end that is fluidly coupled to the second capillary pad 262. Thus, the second fluid 226 flows, via capillary action, from the second reservoir 225, through the capillary passageway 263 of the second capillary tube 261, to the second capillary pad 262 whereby the second capillary pad 262 becomes loaded with the second fluid 226.

In this embodiment, the first and second capillary pads 252, 262 are arranged in the head 120 beneath the cleaning elements in a side-by-side arrangement. Thus, the first capillary pad 252 is positioned on a first side of the longitudinal axis A-A and the second capillary pad 162 is positioned on a second side of the longitudinal axis A-A. Thus, for any tuft hole located on the first side of the longitudinal axis A-A that has a thru-hole as described above, the bristle tuft located within that tuft hole will be fluidly coupled to the first capillary pad 252 (via fibers 258 of the first capillary pad 252 that extend through the thru-hole). Similarly, for any tuft hole located on the second side of the longitudinal axis A-A that has a thru-hole as described above, the bristle tuft located within that tuft hole will be fluidly coupled to the second capillary pad 262 (via fibers 268 of the second capillary pad 262 that extend through the thru-hole).

For example, as shown in FIG. 9C, there is a thru-hole 255 extending from a tuft hole 256 to the first capillary pad 252 and a thru-hole 265 extending from a tuft hole 266 to the second capillary pad 262. A first bristle tuft 257 is positioned within the first tuft hole 256 and a second bristle tuft 267 is positioned within the second tuft hole 266. The fibers 258 of the first capillary pad 252 extend through the thru-hole 255 and directly contact the first bristle tuft 257. The fibers 268 of the second capillary pad 262 extend through the thru-hole 265 and directly contact the second bristle tuft 267. There could be multiple thru-holes coupling the first capillary pad 252 to a first subset of bristle tufts and there could be multiple thru-holes coupling the second capillary pad 262 to a second subset of bristle tufts. In some embodiments, every single one of the bristle tufts that is aligned with the first capillary pad 252 could be fluidly coupled to the first capillary pad 252 via one of the thru-holes 255 and the fibers 258 and every single one of the bristle tufts that is aligned with the second capillary pad 262 could be fluidly coupled to the second capillary pad 262 via one of the thru-holes 265 and the fibers 268. Alternatively, only some of the bristle tufts aligned with each of the first and second capillary pads 252, 262 could be fluidly coupled to the respective one of the first and second capillary pads 252, 262 with the other bristle tufts not being fluidly coupled thereto. As described above, thru-holes such as the first and second thru-holes 255, 265 (or some similar feature that facilitates a fluid coupling between the bristle tufts and the first/second capillary pads 252, 262) should be provided for any bristle tuft that should be fluidly coupled to the capillary pads 252, 262.

In the exemplified embodiment, the first and second capillary pads 252, 262 are spaced apart from one another within the head 120. The reason for this is to ensure that the first fluid 216 loaded onto the first capillary pad 252 does not mix with the second fluid 226 loaded onto the second capillary pad 262 within the first and second capillary pads 252, 262. Rather, in the exemplified embodiment the first and second fluids 216, 226 only mix after being dispensed from the capillary pads 252, 262 to the bristle tufts 257, 267 and from there to a user's oral cavity or other desired application surface.

Although in the exemplified embodiment the first and second capillary pads 252, 262 are arranged in a spaced apart manner on opposite sides of the longitudinal axis A-A, the invention is not to be so limited in all embodiments. The first and second pads 252, 262 can be positioned at any desired location within the head 120 and beneath a subset of the bristle tufts as may be desired to deliver the first and second fluids 216, 226 to various ones of the bristle tufts by capillary action. Thus, the first capillary pad 252 may be positioned along the distal end of the head 120 while the second capillary pad 262 is positioned along the proximal end of the head 120. Alternatively, the first capillary pad 252 may be aligned with the bristle tufts located along a peripheral portion of the bristle field and the second capillary pad 262 may be aligned with the bristle tufts located along a center portion of the bristle field. Any desired arrangement may be used as long as the first capillary pad 252 is fluidly coupled to the first capillary tube 251 and to a first subset of the bristle tufts and the second capillary pad 262 is fluidly coupled to the second capillary tube 261 and to a second subset of the bristle tufts.

Figure 10:
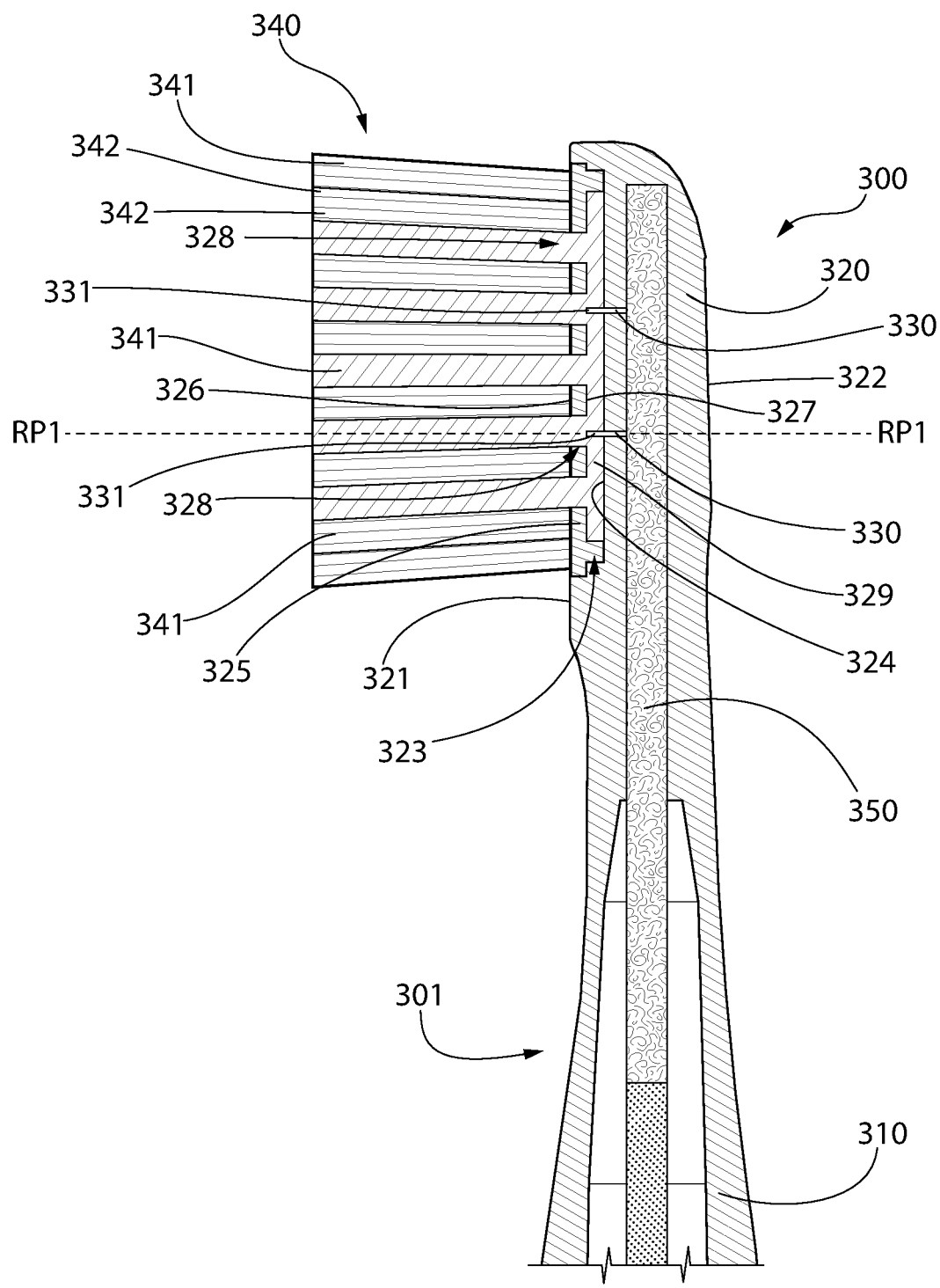
FIG. 10 is the close-up view of FIG. 4A in accordance with an alternative embodiment of the present invention, wherein the cleaning elements are coupled to the head using an anchor free tufting technique.

Referring briefly to FIG. 10, an alternative embodiment of a personal care implement 300 will be described. FIG. 10 is a close-up cross-sectional view that is the same as the view shown in FIG. 4A, except for a different personal care implement. However, the only difference between the personal care implement 300 shown in FIG. 10 and the personal care implement 100 of FIG. 4A is the manner in which the cleaning elements are coupled to the head.

The personal care implement 300 comprises a body 301 comprising a handle 310 and a head 320 and a plurality of cleaning elements 340 extending from the head 320. The handle 310 may be identical to the handle 110 previously described and it may include one or two reservoirs (or more than two reservoirs) much as described above (although not illustrated in FIG. 10). Furthermore, the personal care implement 300 comprises a capillary member 350 for transporting/delivering a fluid from one of the reservoirs to one or more of the cleaning elements 340. This can be achieved with a single-component capillary member (like the capillary member 150 described above) or a two-component capillary member (like the capillary member 160 described above that includes the capillary tube 170 and the capillary pad 180).

The head 320 comprises a front surface 321 and a rear surface 322 opposite the front surface 321. The head 320 comprises a basin cavity 323 formed into the front surface 321, the basin cavity 323 having a floor surface 324. In this embodiment, the cleaning elements 340, which may comprise bristle tufts comprising bristle filaments, are not coupled directly to the head 320 using staples. Rather, in this embodiment, the personal care implement 300 comprises a head plate 325 having a front surface 326 and a rear surface 327 opposite the front surface 326. The head plate 325 has a plurality of tuft holes 328 formed therethrough, each of the tuft holes 328 forming an aperture through the head plate 325 from the front surface 326 to the rear surface 327. Thus, the tuft holes 328 are through holes rather than blind holes. The head plate 325 is a separate and distinct component from the head 320 of the personal care implement 300. However, the head plate 325 is connected to the head 320 at a later stage of the manufacturing process by any suitable technique known in the art, including without limitation thermal or ultrasonic welding, any fusion techniques such as thermal fusion, melting, a tight-fit assembly, a coupling sleeve, threaded engagement, adhesion, or fasteners. Thus, the head plate 325 and the head 320 are separately formed components that are secured together during manufacture of the personal care implement 300.

The cleaning elements 340 comprise a plurality of bristle tufts 341, each of which comprises a plurality of bristle filaments 342. Of course, the cleaning elements 340 may also include rubber bristles, lamella or the like as described above and such features could be injection molded onto the head plate 325. However, at least some of the cleaning elements 340 will be bristle tufts 341 comprising bristle filaments 342. The cleaning elements 340 are coupled to the head 120 in the following manner using a technique known in the art as anchor free tufting or AFT. Specifically, the cleaning elements 340 are arranged into bristle tufts 341, each of the bristle tufts 341 comprising a plurality of the bristle filaments 342. Next, the bristle tufts 341 are inserted into and through the tuft holes 328 so that a first portion of the bristle tuft 341 protrudes from the front surface 326 of the head plate 325 and a second portion of the bristle tuft 341 protrudes from the rear surface 327 of the head plate 325. Next, the second portions of the bristle tuft 341 that are protruding from the rear surface 327 of the head plate 325 are heated to the point of melting, and the second portions of the bristle tuft 341 then forms a melt matte 329 that is adjacent to the rear surface 327 of the head plate 325. The melt matte 329 is a layer of the bristle material that abuts against the rear surface 327 of the head plate 325. The melt matte 329 connects the second ends of the bristle tufts 341 together, which prevents the bristle tufts 341 from being pulled through the tuft holes 328.

Next, the head plate 325 is positioned into the basin cavity 323 of the head 320 so that the melt matte 329 rests atop of the floor 324 of the basin cavity 323. In this manner, the melt matte 329 becomes trapped between the rear surface 327 of the head plate 325 and the floor 324 of the basin cavity 323. The head plate 325 is then coupled to the head 320 using any desired technique, including ultrasonic welding, adhesive, mechanical fasteners or hardware, or the like.

In this embodiment, the head 320 comprises thru-holes 330 that extend from the capillary member 350 (or from the channel in the head 320 in which the capillary member 350 is located) to the floor 324 of the basin cavity 323. Thus, the thru-holes 330 form a passageway from the capillary member 350 to the basin cavity 323 so that the fluid loaded onto the capillary member 350 can be delivered to the cleaning elements 340.

However, the bristle tufts 341 that are melted together to form the melt matte 329 are formed from plastic such as nylon. However, the melt matte 329 is generally porous such that it has many small openings therein that are not controlled for in the melt process. Thus, although this enables the fluid to flow through the melt matte 329 to the bristle tufts 341, it does not allow for specific bristle tufts 341 to be targeted. Rather, the fluid would potentially flow to all of the bristle tufts 341.

In some embodiments, a sealing layer could be provided over the bottom of the melt matte 329 so that the melt matte 329 is no longer porous. In such embodiments, the melt matte 329 may be non-porous so when the melt matte 329 covers the floor 324 of the basin cavity 323 or portions thereof as shown in FIG. 10, the melt matte 329 also covers the openings into the thru-holes 330 and prevents fluid from flowing into and through the thru-holes 330. Therefore, in order to ensure that a fluid pathway exists from the capillary member 350 to the bristle tufts 341, a plurality of second thru-holes 331 may be formed into the melt matte 329 at locations ensuring that each of the second thru-holes 331 is aligned with one of the bristle tufts 341. The second thru-holes 331 extend from the rear surface of the melt matte 329 to the front surface of the melt matte 329 at locations such that openings of the second thru-holes 331 in the front surface of the melt matte 329 are positioned within or surrounded by one of the bristle tufts 341. This allows the fluid to flow, via capillary action, through the second thru-holes 331 and upwardly along the bristle tufts 341 as described herein.

Even without the sealing layer, the second thru-holes 331 may be added to the melt matte 329. Thus, although the fluid will be able to flow through the porous melt matte 329 such that targeting specific bristle tufts 341 for fluid delivery will not be possible, the addition of the second thru-holes 331 may ensure that a greater volume of the fluid is delivered to the bristle tufts 341 that are aligned with the second thru-holes 331 than to the bristle tufts 341 that are not aligned with the second thru-holes 331. Thus, although the fluid may flow to all of the bristle tufts 341, but a greater volume of the fluid can be targeted for specific ones of the bristle tufts 341.

As seen in FIG. 10, the thru-holes 330 extending from the capillary member 250 to the floor 324 of the basin cavity 323 are aligned with the second thru-holes 331 formed into the melt matte 329. Stated another way, a reference plane RP1 that is transverse to the longitudinal axis of the personal care implement 300 intersects one of the bristle tufts 341, one of the thru-holes 330, and one of the second thru-holes 331. As a result, the fluid that is loaded onto the capillary member 350 flows, via passive capillary action, from the capillary member 350, through the thru-holes 330 and into and through the thru-holes 331 to the bottoms of the bristle tufts 341 that are aligned with the thru-holes 331. The fluid then wicks up the bristle tufts 341 within the spaces between the bristle filaments 342 as has been described in detail above. Thus, the same benefits of passive fluid delivery to the cleaning elements can be achieved regardless of whether the cleaning elements are stapled to the head or coupled to the head using other techniques, such as anchor-free tufting.

Figure 11:
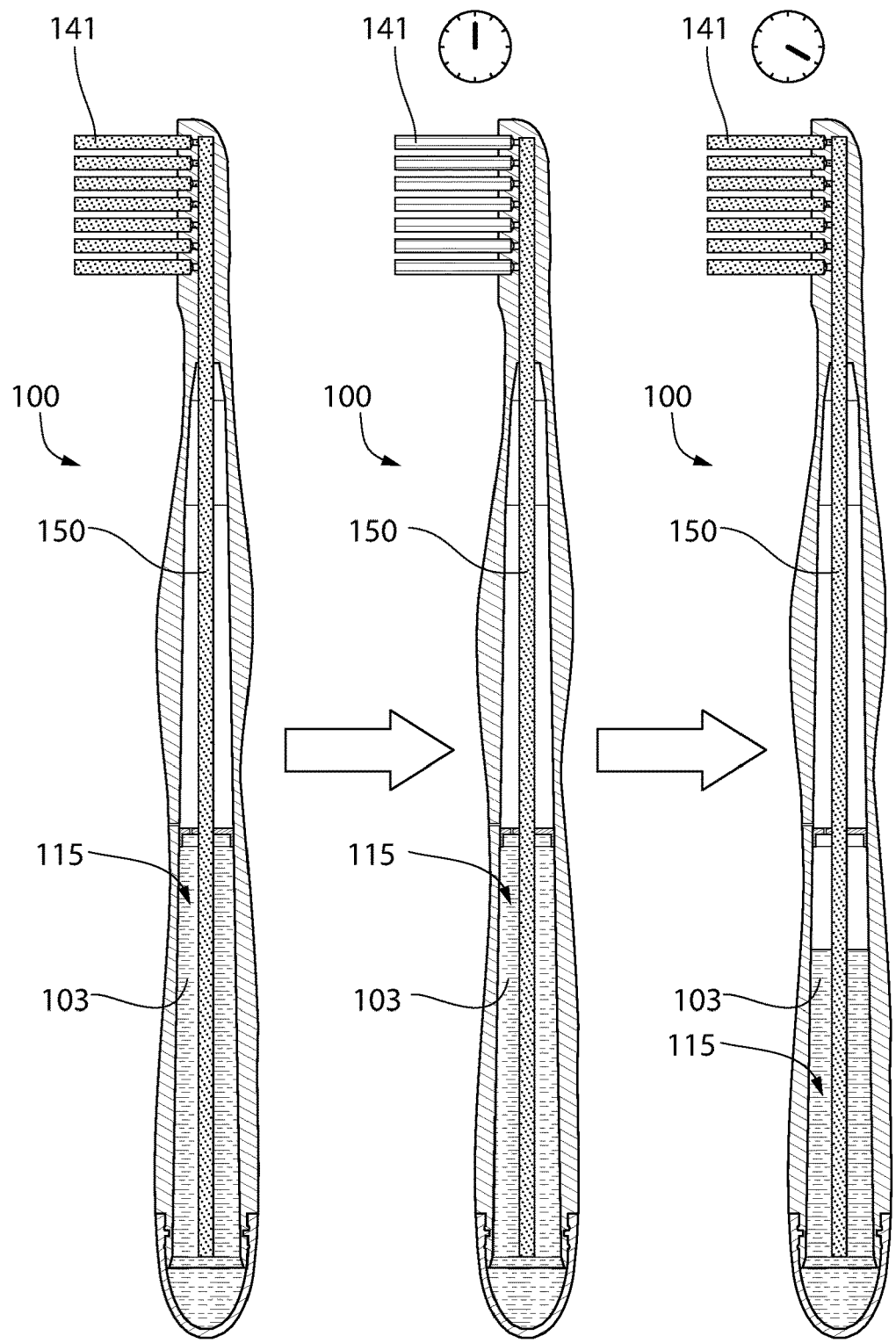
FIG. 11 is several side-by-side cross-sectional views illustrating delivery of a fluid from a reservoir to bristles over a period of time.

FIG. 11 shows the personal care implement 100 three times to illustrate how the fluid 103 flows via capillary action from the reservoir 115 to the cleaning elements 140 over time. Specifically, before use of the personal care implement 100, the fluid 103 is loaded onto the capillary member 150 and into the bristle tufts 141, as shown in the first iteration of the personal care implement 100 in FIG. 11. Next, a user can either rinse the fluid 103 from the bristle tufts 141 or use the personal care implement 100 to clean teeth or other surfaces as desired. This rinsing or use will result in the fluid 103 being removed from the bristle tufts 141 entirely, as shown in the second iteration of the personal care implement 100 in FIG. 11. Next, the personal care implement 100 will be left to sit idly for a period of time, and during this period of time the fluid will flow via passive capillary action back onto the bristle tufts 141, as shown in the third iteration of the personal care implement 100 in FIG. 11. A user will preferably wait a predetermined period of time sufficient to ensure that the bristle tufts 141 become loaded with the fluid 103 to a desired amount before rinsing the bristle tufts 141 again or using the personal care implement 100 for a cleaning activity.

In some embodiments, the fluid 103 may be a sanitizing fluid. The sanitizing fluid may be, for example without limitation, hydrogen peroxide ($H_2O_2$); Sodium bicarbonate ($NaHCO_3$); sodium hypochlorite ($NaClO$); Sodium perborate ($NaH_2BO_4$); and/or Potassium peroxymonosulfate (MPS) ($KHSO_5$). Thus, the personal care implement(s) described herein can be used for passively sanitizing the cleaning elements without a user being required to take any action. Specifically, in between toothbrushing sessions the sanitizing fluid will flow passively via capillary action onto the bristle tufts and into the spaces between the bristle filaments of each of the bristle tufts. This will sanitize the cleaning elements and kill bacteria that otherwise collects thereon. Then, when a user desires to use the personal care implement, the user will first rinse the cleaning elements to remove the sanitizing fluid therefrom (although this step could be omitted in some embodiments particularly if the sanitizing fluid is not harmful to a user). The user may rinse the cleaning elements using a faucet and tap water in some embodiments or the user may use a purified water as the rinse fluid. Next, the user will apply toothpaste onto the cleaning elements and brush the teeth with the cleaning elements in a conventional way. After brushing, the user will allow the personal care implement to rest idly for a period of time during which a volume of the sanitizing fluid will be passively delivered from the reservoir to the bristle tufts, and more specifically to the spaces between the bristle filaments of the bristle tufts, via capillary action. In certain embodiments, the cleaning elements should become fully loaded in less than 12 hours, more specifically less than 10 hours, or less than 8 hours, or less than 6 hours, or less than 4 hours, or less than 2 hours, to ensure that the cleaning elements are adequately sanitized between brushing sessions.

Figure 12:
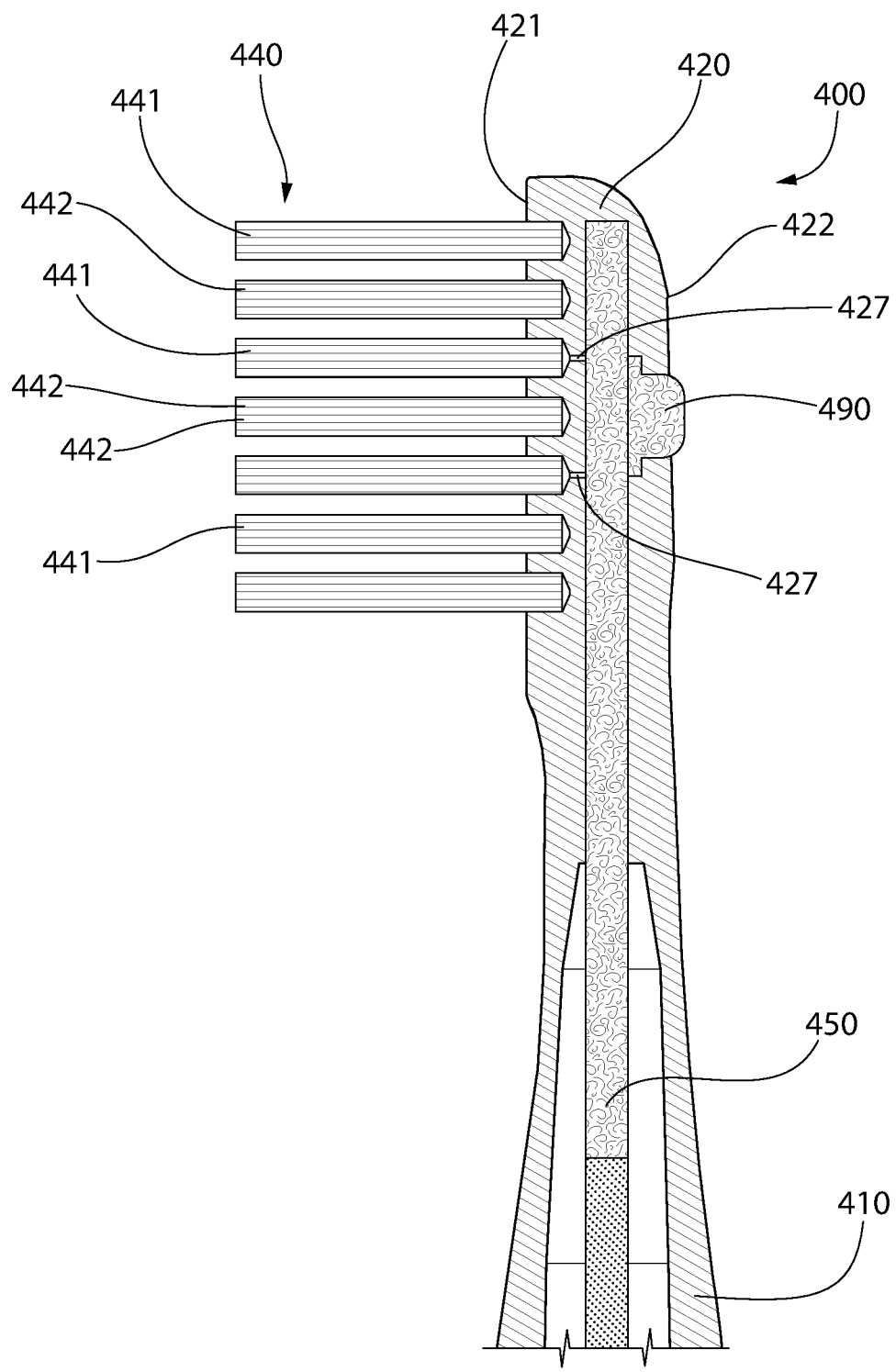
FIG. 12 is the close-up view of FIG. 4A in accordance with another embodiment of the present invention, illustrating an applicator exposed on a rear surface of the head.

FIG. 12 illustrates an alternative embodiment of a personal care implement 400 that is identical to the personal care implement 100 shown in FIG. 4A except the personal care implement 400 also comprises an applicator 490. Specifically, the personal care implement 400 comprises a handle 410 and a head 420, the head 420 having a front surface 421 and a rear surface 422. The personal care implement 400 comprises a plurality of cleaning elements 440 extending from the front surface 421 of the head 420. The plurality of cleaning elements 440 may comprise a plurality of bristle tufts 441, each of which comprises a plurality of bristle filaments 442. The personal care implement 400 also comprises a reservoir (not shown, but the description of the personal care implement 100 above is applicable) and a capillary member 450 fluidly coupled to a fluid held in the reservoir (the reservoir is not shown, but the reservoir 115 illustrated in FIG. 3 along with the corresponding description is applicable). The personal care implement 400 also comprises one or more thru-holes 427 that fluidly couples the capillary member 450 to one or more of the bristle tufts 441. These features, with the exception of the applicator, are all described above with regard to the personal care implement 100.

In this embodiment, the personal care implement 400 comprises the applicator 490 in addition to the above-noted features. The applicator 490 may be formed from a fibrous wicking material such as, for example without limitation, a porous material, a fibrous material, a foam material, or the like (i.e., any other material described above as possibly forming the capillary member 150). The applicator 490 is fluidly coupled to the capillary member 450 and protrudes from the rear surface 422 of the head 420 through an opening in the rear surface 422 of the head 420. Thus, the applicator 490 is exposed on or along the rear surface 422 of the head 420. Thus, the fluid can be delivered from the reservoir to the capillary member 450 and from the capillary member 450 to the applicator 490 for application to a user's oral cavity or other surfaces. During use, as the rear surface 422 of the head 420 contacts oral surfaces in the oral cavity, the fluid will be dispensed from the applicator 490 into the oral cavity. In some embodiments, the fluid coupling between the bristle tufts 441 and the capillary member 450 may not exist, but the applicator 490 may be the only pathway for dispensing the fluid. In other embodiments, the personal care implement 400 may include fluid couplings from the capillary member 450 to a subset of the bristle tufts 441 as described above with regard to the previously disclosed embodiments and to the applicator 490 as depicted in FIG. 12.

Figure 13A:
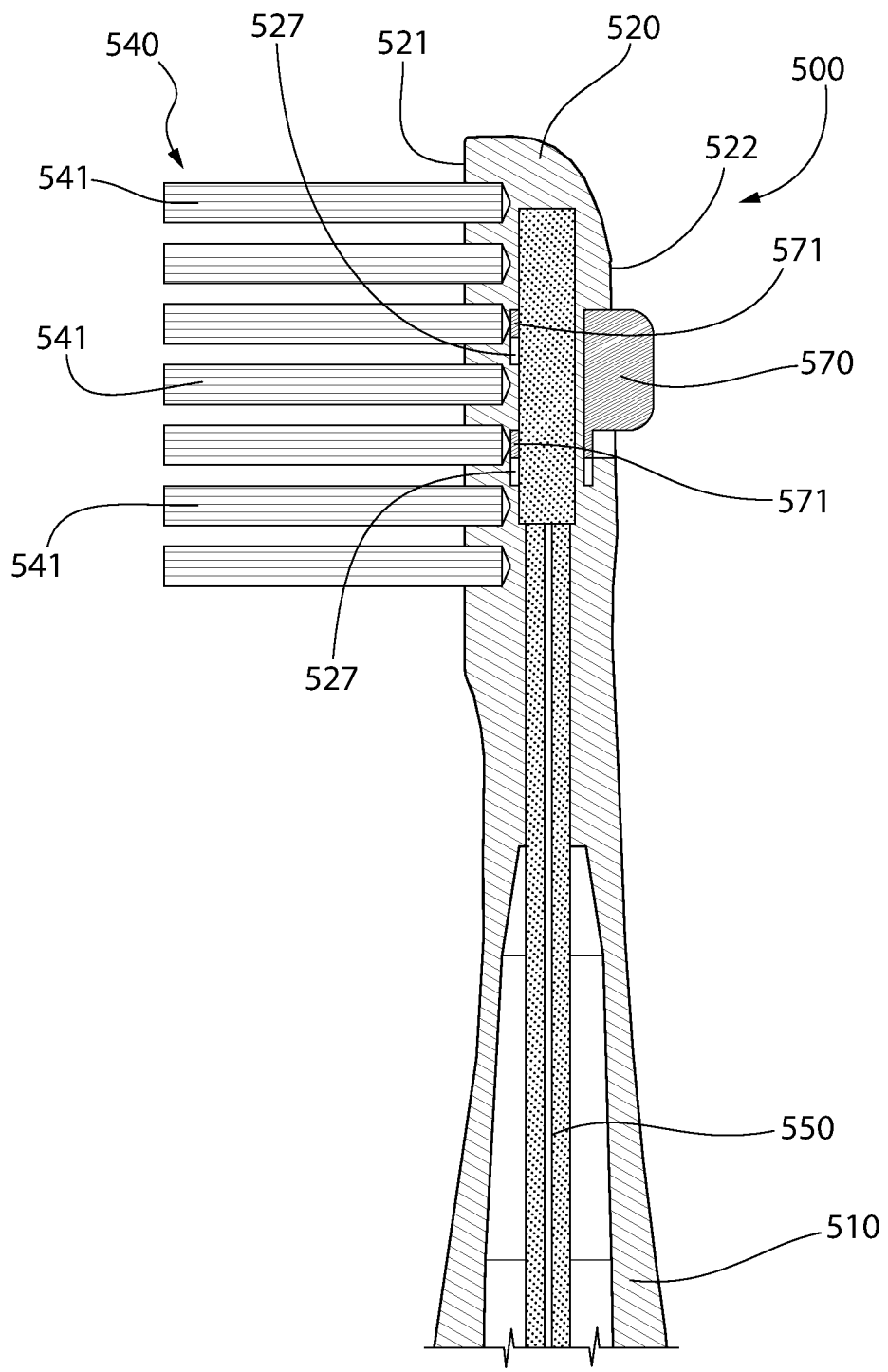
FIG. 13A is the close-up view of FIG. 6A in accordance with another embodiment of the present invention, illustrating a movable barrier in an open state.
Figure 13B:
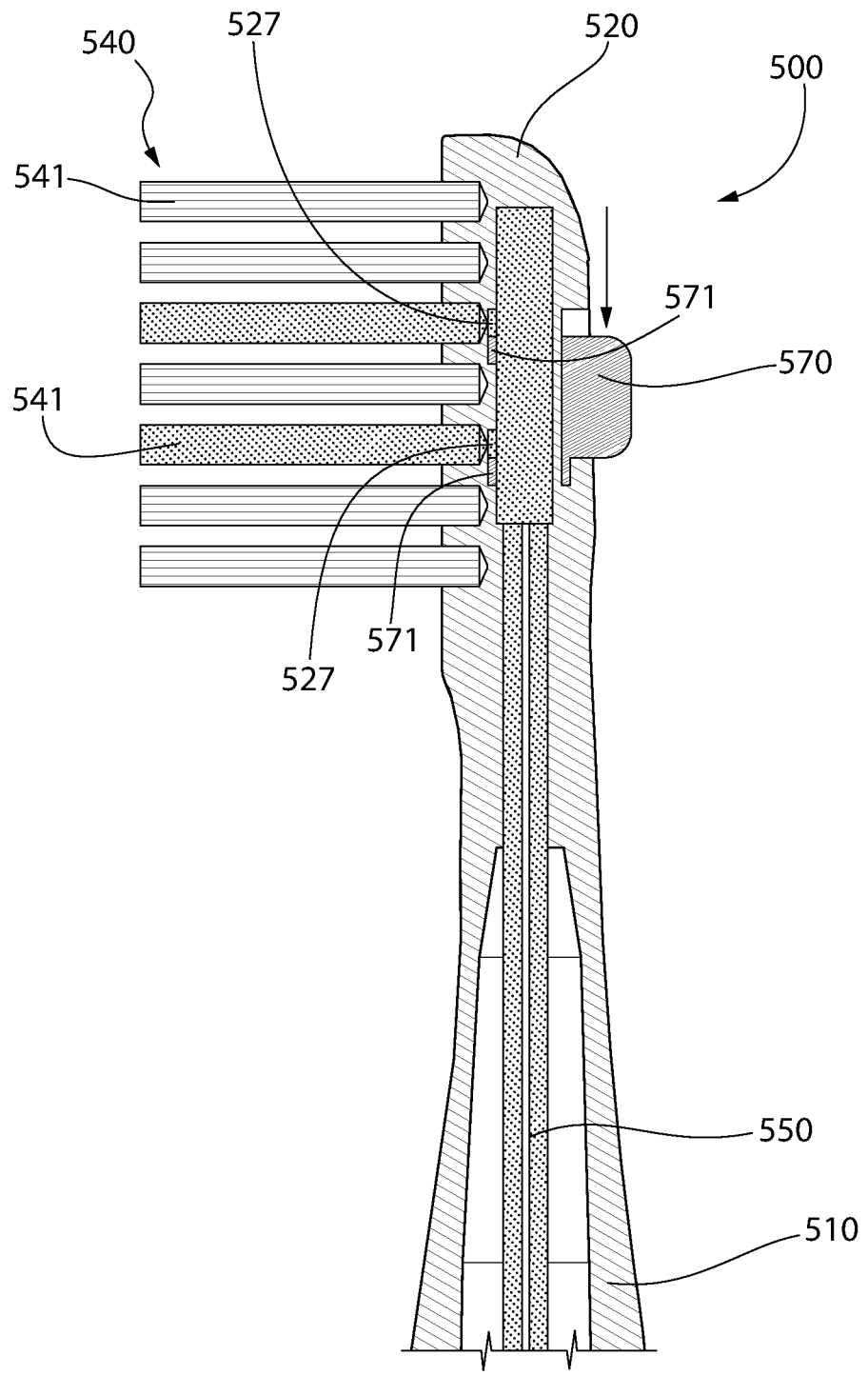
FIG. 13B is the close-up view of FIG. 13A illustrating the movable barrier in a closed state.

Referring to FIGS. 13A and 13B, yet another embodiment of a personal care implement 500 will be described. The personal care implement 500 is identical to the personal care implement 100 depicted in FIGS. 6A-6C except that the personal care implement 500 includes some additional features. The personal care implement 500 comprises a handle 510 having a reservoir with a fluid therein (not shown, but any of the previously described embodiments are applicable) and a head 520 coupled to the handle 510. The head 520 has a front surface 521 and a rear surface 522 opposite the front surface 520. A plurality of cleaning elements 540 extend from the front surface 521 of the head 520. The personal care implement 500 also comprises a capillary member 550 that is fluidly coupled to the fluid in the reservoir and to one or more bristle tufts 541 of the cleaning elements 540. Specifically, a plurality of thru-holes 527 extend from some of the bristle tufts 541 to the capillary member 550 thereby fluidly coupling those bristle tufts 541 to the capillary member 550.

In this embodiment, the personal care implement 500 also comprises a movable barrier 571 positioned within each of the thru-holes 527. Of course, there may be movable barriers 571 positioned in some of the thru-holes 527 but not all of them in alternative embodiments. Each of the movable barriers 571 is operably coupled to an actuator 570. In the exemplified embodiment, each of the movable barriers 571 is operably coupled to the same actuator 570, but in other embodiments each of the movable barriers may be operably coupled to its own actuator 570.

As seen in FIGS. 13A and 13B, a user can manipulate the actuator 570 to move the movable barriers 571 between: (1) an open state, illustrated in FIG. 13B, whereby the bristle tuft 541 associated with that particular movable barrier 571 is fluidly coupled to the capillary member 550 and (2) a closed state, illustrated in FIG. 13A, whereby the bristle tuft 541 is not fluidly coupled to the capillary member 550 because the movable barrier 571 closes the thru-hole 527. Thus, movement of the movable barrier 571 opens and closes the thru-holes 527, which in turn permits and prevents fluid communication between the capillary member 550 and the bristle tufts 541. Thus, movement or manipulation of the actuator 570 moves the movable barrier 571 so that in one position it cuts off fluid communication between the bristle tuft 541 and the capillary member 550 and in another position it opens fluid communication between the bristle tuft 541 and the capillary member 550. This adds another level of control to the user, such that the user can decide whether he/she wants to dispense the fluid to the bristle tufts 541 and for how long. In the exemplified embodiment, the actuator 570 is a slidable mechanism, but this concept could be achieved with other actuator mechanisms, including electro-mechanical devices, push buttons, or the like.

In some embodiments, the invention may be directed to a method of preparing a toothbrush, which could be any of the personal care implements 100, 200, 400, 500 described herein, for cleaning an oral cavity. This method will be described with reference to FIGS. 1-6C and the reference numerals used in those figures, but it should be appreciated that the methods are also applicable to the other embodiments described herein.

The method of preparing a toothbrush may include providing the toothbrush 100, 200, 400, 500 comprising a reservoir 115 containing a store of a fluid 103 and a plurality of bristle tufts 141. Each of the bristle tufts 141 may comprise a plurality of bristle filaments 142 as described herein with the bristle filaments 142 being arranged so that spaces exist between the bristle filaments. Next, the method may include passively delivering the fluid 103 from the reservoir 115 to one or more of the bristle tufts 141 via capillary action. This passive delivery comprises the fluid 103 wicking upwardly within the spaces between the bristle filaments 142 of each of the one or more bristle tufts 141. Next, a user may apply a toothpaste to the bristle tufts 141 and brush the oral cavity, including the teeth, with the bristle tufts 141 with the toothpaste thereon.

In other embodiments, the invention may be directed to a method of whitening teeth utilizing any of the personal care implements 100, 200, 400, 500 described herein. This method will be described with reference to FIGS. 1-6C and the reference numerals used in those figures, but it should be appreciated that the methods are also applicable to the other embodiments described herein.

There are toothpastes and dentifrices on the market that include hydrogen peroxide as a whitening agent and these toothpastes are marketed as tooth whitening toothpastes. However, they suffer from certain deficiencies. Specifically, it is known that the efficacy of hydrogen peroxide bleaching is directly proportional to the increase in its pH. However, in order to maximize shelf-life of hydrogen peroxide-containing formulations, the pH is often set to a lower level, at which the peroxide is more stable but where the whitening efficacy is not optimal. Using these toothpastes without first increasing the pH results in a less than optimum tooth whitening result. Thus, the invention may, in some embodiments, be directed to curing this problem by storing a buffer solution (as the fluid 103) in the reservoir and delivering the buffer solution to the cleaning elements (or applicator) so that it mixes with the hydrogen peroxide containing toothpaste during toothbrushing. This offers the unique ability to increase the pH of a hydrogen peroxide toothpaste directly at the point of contact with the teeth, thereby increasing the bleaching effect of the toothpaste to be greater than that of a similar toothpaste with a lower pH, without impacting its shelf-life.

Thus, in some embodiments the invention may be a method of whitening teeth and it will be described with the numbering used in FIGS. 1-6C, it being appreciated that the method is also applicable to the other structural embodiments of the personal care implement disclosed herein. The method may comprise providing a toothbrush 100 comprising a plurality of cleaning elements 140 and a reservoir 115 containing a store of a buffer solution (as the first fluid 103). The buffer solution 103 may be selected from the group consisting of Sodium bicarbonate ($NaHCO_3$) and sodium carbonate ($Na_2CO_3$), although this list is non-exhaustive.

Next, the method includes delivering the buffer solution 103 from the reservoir 115 to one or more of the cleaning elements 140 via capillary action. In some embodiments, this can be achieved passively without any action required by the user, as described herein, as the buffer solution 103 may flow through various capillary components of the toothbrush 100. However, the invention is not to be so limited in all embodiments. Thus, in this particular embodiment, the buffer solution 103 may be delivered to the cleaning elements 140 in other ways. For example, in some embodiments the buffer solution 103 may be pumped into the cleaning elements 140 via an applied positive pump pressure. There may be a resilient area on the handle and a user can apply pressure onto that resilient area to pump the buffer solution 103 from the reservoir 115 to the cleaning elements 140. Of course, other pumps may be used including electrical pumps, electro-mechanical pumps, or the like.

Next, a toothpaste that contains hydrogen peroxide may be applied to the cleaning elements 140 of the toothbrush. Such a toothpaste may have a first pH that is less than a third pH of the buffer solution 103. Finally, the method includes brushing the teeth with the tooth cleaning elements 140 that have the buffer solution 103 therein (due to the wicking action) and the toothpaste thereon. During such brushing, the buffer solution 103 mixes with the toothpaste to form a tooth whitening mixture that has a second pH that is greater than the first pH. In some embodiments, the second pH, which is the pH of the tooth whitening mixture formed by mixing the toothpaste with the buffer solution 103, may be in a range of 10 to 11, or more specifically 10.2 to 10.8, or more specifically 10.4-10.6. In some embodiments, the tooth whitening mixture may include 21.2% by weight $Na_2CO_3$ (or a range of 18-24% by weight $Na_2CO_3$). In other embodiments, the tooth whitening mixture may include 8.4% by weight $NaHCO_3$ (or a range of 6-11% by weight $NaHCO_3$). Because the pH is increased, the efficacy of the hydrogen peroxide in the toothpaste is increased. Thus, this invention improves the efficacy of a hydrogen peroxide containing toothpaste at the point of use during a toothbrushing session.

Although described herein with the buffer solution 103 flowing to the cleaning elements, this is not required in all embodiments. In other embodiments, the buffer solution 103 may flow to an applicator, such as the applicator 490 described above with reference to FIG. 12, to dispense the buffer solution 103 into the oral cavity during use of the toothbrush. In such an embodiment, the buffer solution will still mix with the hydrogen peroxide containing toothpaste during use to increase the pH of the hydrogen peroxide containing toothpaste, thereby increasing its efficacy in tooth whitening.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A method of whitening teeth comprising:
   delivering a buffer solution from a reservoir of a toothbrush to one or more tooth cleaning elements of the toothbrush;
   applying a toothpaste containing a peroxide to the one or more tooth cleaning elements, the toothpaste having a first pH; and
   brushing the teeth with the one or more tooth cleaning elements, thereby mixing the buffer solution and the toothpaste to form, at surfaces of the teeth, a tooth whitening mixture having a second pH that is greater than the first pH;
   wherein delivering the buffer solution from the reservoir to the one or more tooth cleaning elements comprises flowing the buffer solution through a capillary member that is fluidly coupled to the reservoir and to the one or more tooth cleaning elements;
   wherein each of the one or more tooth cleaning elements comprises a plurality of bristle tufts, each of the plurality of bristle tufts comprising a plurality of bristle filaments; and
   wherein the capillary member comprises a main body and a plurality of fibers extending between the main body and the plurality of bristle filaments of a bristle tuft of the plurality of bristle tufts.

2. The method according to claim 1, wherein the buffer solution wicks upwardly along the one or more of the tooth cleaning elements within spaces between the plurality of bristle filaments via capillary action.

3. The method according to claim 2 wherein the plurality of bristle filaments are non-hollow and formed from a non-porous material such that the buffer solution cannot pass through or along the plurality of bristle filaments individually.

4. The method according to claim 1 wherein the buffer solution has a third pH that is greater than the first pH.

5. The method according to claim 1 wherein the buffer solution is selected from the group consisting of Sodium carbonate and Sodium bicarbonate.

6. The method according to claim 1 wherein the peroxide is hydrogen peroxide.

7. A method of whitening teeth comprising:
   delivering a buffer solution from a reservoir of an oral care implement to tooth cleaning elements of the oral care implement;
   applying a toothpaste containing a peroxide to the tooth cleaning elements of the oral care implement, the toothpaste having a first pH; and
   brushing teeth with the tooth cleaning elements, thereby mixing the buffer solution and the toothpaste to form, at surfaces of the teeth, a tooth whitening mixture having a second pH that is greater than the first pH;
   wherein delivering the buffer solution from the reservoir to the tooth cleaning elements comprises flowing the buffer solution through a capillary member, the capillary member comprising a main body and a plurality of fibers extending between the main body and a plurality of bristle filaments of a bristle tuft of the tooth cleaning elements.

8. The method according to claim 7 wherein the buffer solution is delivered from the reservoir to the tooth cleaning elements by capillary action.

9. The method according to claim 7 wherein the buffer solution wicks upwardly along the bristle tuft within spaces between the plurality of bristle filaments.

10. The method according to claim 9 wherein the plurality of bristle filaments are non-hollow and formed from a non-porous material such that the buffer solution cannot pass through or along the plurality of bristle filaments individually.

11. The method according to claim 7 wherein the buffer solution has a third pH that is greater than the first pH.

12. The method according to claim 7 wherein the buffer solution is selected from the group consisting of Sodium bicarbonate and Sodium carbonate.

13. The method according to claim 7 wherein the peroxide is hydrogen peroxide.

* * * * *